United States Patent
Li et al.

(10) Patent No.: US 10,973,251 B1
(45) Date of Patent: Apr. 13, 2021

(54) NUTRITIONAL TREATMENT FOR CANCER

(71) Applicant: The Board of Trustees of the Leland Stanford Junior University, Stanford, CA (US)

(72) Inventors: Xiyan Li, Mountain View, CA (US); Michael Snyder, Stanford, CA (US); Xin Wang, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 15/762,032

(22) PCT Filed: Sep. 20, 2016

(86) PCT No.: PCT/US2016/052720
§ 371 (c)(1),
(2) Date: Mar. 21, 2018

(87) PCT Pub. No.: WO2017/053328
PCT Pub. Date: Mar. 30, 2017

Related U.S. Application Data

(60) Provisional application No. 62/221,589, filed on Sep. 21, 2015.

(51) Int. Cl.
| | | |
|---|---|---|
| *A23L 33/00* | (2016.01) | |
| *A61P 35/00* | (2006.01) | |
| *A61K 31/185* | (2006.01) | |
| *A61K 31/675* | (2006.01) | |
| *G01N 33/50* | (2006.01) | |
| *A61K 31/525* | (2006.01) | |

(52) U.S. Cl.
CPC ............... *A23L 33/30* (2016.08); *A23L 33/40* (2016.08); *A61K 31/185* (2013.01); *A61K 31/525* (2013.01); *A61K 31/675* (2013.01); *A61P 35/00* (2018.01); *G01N 33/5008* (2013.01); *A23V 2002/00* (2013.01)

(58) Field of Classification Search
CPC ....... A23L 33/30; A23L 33/40; A61K 31/675; A61K 31/185; A61K 31/525; G01N 33/5008; A61P 35/00; A23V 2002/00
See application file for complete search history.

(56) References Cited

U.S. PATENT DOCUMENTS

| | | |
|---|---|---|
| 3,024,167 A | 3/1962 | Damaskus |
| 4,988,724 A | 1/1991 | Ajani et al. |
| 5,597,805 A | 1/1997 | Breborowicz et al. |
| 5,776,503 A | 7/1998 | Martis et al. |
| 6,274,103 B1 | 8/2001 | Taylor |
| 6,399,381 B1 | 6/2002 | Blum et al. |
| 2003/0013765 A1 | 1/2003 | Veech |
| 2008/0221497 A1 | 9/2008 | Haik, Jr. |
| 2008/0255499 A1 | 10/2008 | Kim |
| 2010/0187476 A1 | 7/2010 | Yugari et al. |
| 2010/0317602 A1 | 12/2010 | Moore |
| 2011/0229521 A1 | 9/2011 | Schiffrin et al. |
| 2014/0235569 A1 | 8/2014 | Halevie-Goldman |

FOREIGN PATENT DOCUMENTS

| | | |
|---|---|---|
| AU | 2016326347 A1 | 5/2018 |
| CA | 3033333 A1 | 3/2017 |
| CN | 103652926 A | 3/2014 |
| CN | 108777999 A | 11/2018 |
| EP | 3352586 A1 | 8/2018 |
| JP | 2018532398 A | 11/2018 |
| WO | 2013011166 A2 | 1/2013 |
| WO | 2014197533 A2 | 12/2014 |
| WO | 2015/031735 A1 | 3/2015 |
| WO | 2017053328 A1 | 3/2017 |
| WO | 2017144877 A1 | 8/2017 |
| WO | 2019118519 A1 | 6/2019 |

OTHER PUBLICATIONS

Goseki et al., Tohoku J. exp. Med., 1987, vol. 151, 191-200.*
Ooi et al., Archives of Medical Research, 2004, vol. 35, p. 289-293.*
Samel et al., Cancer Gene Therapy, 2006, vol. 13, p. 65-73.*
Durando et al., Oncology, 2010, vol. 78, No. 3-4, p. 205-209, Abstract Only.*
Courtney-Martin et al., Nutrition Reviews, 2012, vol. 70, No. 3, p. 170-175.*
Miller et al. (2002) Oxidation of the glutathione/glutathione disulfide redox state is induced by cysteine deficiency in human colon carcinoma HT29 cells Journal of Nutrition 132:2303-2306.
Street et al. (1941) Some Effects Produced by Long-Continued Subminimal Intakes of Vitamin B(1) Yale J. Biol. Med. 13:293-308.
Lauterberg et al. (1994) Depletion of total cysteine, glutathione, and homocysteine in plasma by ifosfamide/mesna therapy. Cancer Chemother Pharmacol 35:132-136.
Scott et al. (2000) Single amino acid (arginine) deprivation: rapid and selective death of cultured transformed and malignant cells. Br. J. Cancer 83:800-810.
PCT/US2016/052720 International Search Report.
Extended European Search Report for European Application No. 16849444.1, Search completed Apr. 4, 2019, dated Apr. 12, 2019, 12 Pgs.
International Preliminary Report on Patentability for International Application PCT/US2016/052720, Report dated Mar. 27, 2018, dated Apr. 5, 2018, 12 Pgs.
Courtney-Martin et al., "Methionine-Adequate Cysteine-Free Diet Does Not Limit Erythrocyte Glutathione Synthesis in Young Healthy Adult Men", The Journal of Nutrition, vol. 138, No. 11, Nov. 1, 2008, pp. 2172-2178.

(Continued)

*Primary Examiner* — Kade Ariani
(74) *Attorney, Agent, or Firm* — KPPB LLP

(57) ABSTRACT

Methods of screening cancerous cells for nutritional weaknesses and methods of treating cancer nutritionally are disclosed. Certain cancers depend on being supplied with one or more nutrients that are non-essential for normal cells. In particular, the invention relates to methods of treating cancer by identifying nutritional weaknesses of cancer cells and using nutritional therapy to suppress cancer by putting a subject on a diet that deprives cancerous cells of a nutrient needed for cancer proliferation and growth. Nutritional therapy can be used to enhance the effectiveness of current cancer treatments.

24 Claims, 29 Drawing Sheets

(56) References Cited

OTHER PUBLICATIONS

Miller et al., "Oxidation of the Glutathione/Glutathione Disulfide Redox State Is Induced by Cysteine Deficiency in Human Colon Carcinoma HT29 Cells", The Journal of Nutrition, vol. 132, No. 8, Aug. 2002, pp. 2303-2306.
Tang et al., "Cystine Deprivation Triggers Programmed Necrosis in VHL-Deficient Renal Cell Carcinomas", Cancer Research, vol. 76, No. 7, Apr. 1, 2016, pp. 1892-1903.
Google Patent Search: "dialysis solution glucose vitamin arginine", Jul. 14, 2020, 2 pgs.
Google Scholar Search: "dialysis solution dextrose vitamin arginine", Jul. 14, 2020, 2 pgs.
International Search Report and Written Opinion for International Application No. PCT/US2018/065045, Search completed Apr. 17, 2019, dated Apr. 30, 2019, 17 pgs.
Office Action for U.S. Appl. No. 16/897,152, dated Aug. 6, 2020, 18 pgs.
Prior Art Web Search History, Generated on Jul. 16, 2020, 1 pg.
"MDA-MB-453 (ATCC HTB-131)", American Type Culture Collection (ATCC) Product Catalog, ATCC Product Catalog MDA-MB-453 (ATCC® HTB-131™) Retrieved Online at URL: https://www.atcc.org/products/all/HTB-131.aspx#characteristics, 2020, 2 pages.
Baron et al., "Letter: Glucose is dextrose is glucose", British Medical Journal, vol. 2, No. 6026, Jul. 3, 1976, pp. 41-42.
Cairns et al., "Regulation of cancer cell metabolism", Nature Reviews Cancer, vol. 11, Jan. 24, 2011, pp. 85-95.
Drexler et al., "Malignant hematopoietic cell lines: in vitro models for the study of MLL gene alterations", Leukemia, vol. 18, Dec. 4, 2003, pp. 227-232.
Gazdar et al., "Lung Cancer Cell Lines as Tools for Biomedical Discovery and Research", Journal of the National Cancer Institute, vol. 102, No. 17, Sep. 8, 2010, pp. 1310-1321.
Hall et al., "MDA-MB-453, an Androgen-responsive Human Breast Carcinoma Cell Line Wth High Level Androgen Receptor Expression", European Journal of Cancer, vol. 30A, No. 4, 1994, pp. 484-490.
Hanahan et al., "Hallmarks of Cancer: The Next Generation", Cell, vol. 144, No. 5, Mar. 4, 2011, pp. 646-674.
Li et al., U.S. Appl. No. 16/897,152, filed Jun. 9, 2020, 111 pgs.
Linnoila, "Spectrum of neuroendocrine differentiation in lung cancer cell lines featured by cytomorphology, markers, and their corresponding tumors", Journal of Cellular Biochemistry, vol. 63, No. S24, Supplement: NCI—Navy Medical Oncology Branch Cell Line Supplement, 1996, pp. 92-106.
Maddocks et al., "Serine starvation induces stress and p53-dependentmetabolic remodelling in cancer cells", Nature, vol. 493, Jan. 24, 2013, pp. 542-546, first published Dec. 16, 2012, doi:10.1038/nature11743.
Mitra et al., "Technologies for deriving primary tumor cells for use in personalized cancer therapy", Trends in Biotechnology, vol. 31, No. 6, Jun. 1, 2013, pp. 347-354.
Moore et al., "An androgen receptor mutation in the MDA-MB-453 cell line model of molecular apocrine breast cancer compromises receptor activity", Endocrine-Related Cancer, vol. 19, No. 4, Jul. 22, 2012, pp. 599-613.
Mouradov et al., "Colorectal Cancer Cell Lines Are Representative Models of the Main Molecular Subtypes of Primary Cancer", Molecular and Cellular Pathobiology, vol. 74, No. 12, Jun. 15, 2014, pp. 3238-3247.
Neve et al., "A collection of breast cancer cell lines for the study of functionally distinct cancer subtypes", Cancer Cell, vol. 10, No. 6, Dec. 1, 2006, pp. 515-527.
Saiselet et al., "Thyroid cancer cell lines: an overview", Frontiers in Endocrinology, vol. 3, No. 133, Nov. 16, 2012, 9 pgs.
Sheen et al., "Defective Regulation of Autophagy upon Leucine Deprivation Reveals a Targetable Liability of Human Melanoma Cells In Vitro and In Vivo", Cancer Cell, vol. 19, No. 5, May 17, 2011, pp. 613-628.
Sobel et al., "Cell Lines Used in Prostate Cancer Research: A Compendium of Old and New Lines—Part 1", Journal of Urology, vol. 173, No. 2, Feb. 2005, pp. 342-359.
Vander Heiden, "Targeting cancer metabolism: a therapeutic window opens", Nature Reviews Drug Discovery, vol. 10, Aug. 31, 2011, pp. 671-684.
Young, "Adult Amino Acid Requirements: The Case for a Major Revision in Current Recommendations", The Journal of Nutrition, vol. 124, No. Supp. 8, Aug. 1, 1994, pp. 1517S-1523S.
Zheng et al., "Establishment and characterization of primary lung cancer cell lines from Chinese population", Acta Pharmacologica Sinica, vol. 32, Mar. 4, 2011, pp. 385-392.

* cited by examiner

NUTRITIONAL TREATMENT FOR CANCER

STATEMENT REGARDING FEDERALLY SPONSORED RESEARCH OR DEVELOPMENT

This invention was made with Government support under contract GM062480 awarded by the National Institutes of Health. The Government has certain rights in the invention.

TECHNICAL FIELD

The present invention pertains generally to methods of treating cancer. In particular, the invention relates to methods of treating cancer by identifying nutritional weakness of cancer cells and using nutritional therapy to suppress cancer growth.

BACKGROUND

Cancer is a group of deadly diseases that are widespread and largely incurable. Current treatments are both costly and have variable efficacy. Cancer cells are known to adopt a distinctive type of metabolism, called the Warburg effect, which involves uncoupled cellular glycolysis and mitochondrial aerobic respiration (Hanahan et al. (2011) Cell 144(5): 646-674; Cairns et al. (2011) Nat. Rev. Cancer 11 (2):85-95). The resultant metabolic imbalance may cause inefficient flux control and biosynthesis, which in turn lead to requirements for certain nutrients that are not necessary for normal cells. Sporadic studies have explored this aspect of cancer (Maddocks et al. (2013) Nature 493(7433):542-546; Sheen et al. (2011) Cancer Cell 19(5):613-628), but no one has tested this in a systematic way.

Thus, there remains a need in the art for identifying nutritional weakness of cancer cells that can be exploited to improve current methods of treating cancer.

SUMMARY

In particular, the invention relates to methods of treating cancer by identifying nutritional weaknesses of cancer cells and using nutritional therapy to suppress cancer growth.

In one aspect, the invention includes a method of identifying a nutritional weakness of a cancerous cell, the method comprising: a) culturing the cancerous cell in media having all essential nutrients for growth of a normal cell, but lacking at least one nutrient that is nonessential for growth of the normal cell, but possibly needed for growth of the cancerous cell; and b) measuring growth of the cancerous cell, wherein suppression of growth of the cancerous cell in the media indicates that the cancerous cell has the nutritional weakness, wherein growth of the cancerous cell is dependent on at least one nutrient that is nonessential for growth of the normal cell. The cancerous cell to be screened for nutritional weaknesses may be obtained from a cancer cell line or a biological sample from a subject who has cancer (e.g., tumor biopsy or bodily fluid, such as blood or urine comprising cancerous cells). This method can be used to identify diet-responsive cancers, wherein depriving the cancer of one or more nutrients identified by screening suppresses growth and proliferation of the cancer, or more preferably, induces cell death.

Once a nutritional weakness of a cancer is identified by the methods described herein, a subject may be treated for the cancer by putting the subject on a diet that reduces or eliminates the subject's daily intake of foods containing at least one nutrient associated with the nutritional weakness of the cancer. Nutritional therapy may be implemented by providing the subject with dietary instructions on reducing or eliminating daily intake of one or more nutrients associated with the nutritional weaknesses of the cancer. Alternatively, the subject may be provided with meals (e.g., breakfast meals, lunch meals, dinner meals, or snacks) that do not contain or have low amounts of one or more nutrients associated with the nutritional weaknesses of the cancer. In certain embodiments, the diet reduces the subject's daily intake of foods containing one or more nutrients associated with nutritional weaknesses of the cancer by at least 70% to 100%, including any percent within this range, such as 70, 75, 80, 85, 90, 95, 96, 97, 98, 99, or 100%. Preferably, the diet provides other nutrients at levels in accordance with United States Recommended Daily Allowances (USRDA) guidelines.

In certain embodiments, a cancerous cell has a nutritional weakness such that growth and proliferation of the cancerous cell is dependent on at least one amino acid that is nonessential for growth of a normal cell. In certain embodiments, the cancerous cell is dependent on at least one amino acid selected from the group consisting of cysteine, arginine, glutamine, serine, and tyrosine.

In another embodiment, the invention includes a method of identifying and treating a subject having a diet-responsive cancer, the method comprising: a) obtaining a biological sample comprising cancerous cells from the subject, b) culturing the cancerous cells in test media having all essential amino acids for growth of a normal cell, but deficient in one or more amino acids that are nonessential for growth of the normal cell, but possibly needed for growth of the cancerous cells; and c) measuring growth of the cancerous cells, wherein suppression of growth of the cancerous cells in the test media indicates that the cancer can be treated by removal of one or more amino acids needed for growth of the cancerous cells from the subject's diet, and d) treating the subject for the cancer by putting the subject on a diet that reduces or eliminates the subject's daily intake of one or more amino acids needed for growth of the cancerous cells.

In another embodiment, the subject is put on a protein-free or low-protein diet and further administered an amino acid-containing supplement comprising all of the essential amino acids (i.e., histidine, isoleucine, leucine, lysine, methionine, phenylalanine, threonine, tryptophan, and valine) The amino acid-containing supplement may further comprise one or more nonessential amino acids selected from the group consisting of alanine, arginine, asparagine, aspartate, glutamate, glutamine, glycine, proline, serine, and tyrosine, provided that the amino acid-containing supplement does not contain any of the nonessential amino acids identified by the methods described herein as needed for growth of the cancer for which the individual is undergoing therapy. In one embodiment, the amino acid-containing supplement does not contain cysteine or cystine.

Nutritional therapy should be continued long enough to bring about a positive therapeutic response with respect to treatment of an individual for a particular cancer, such as an anti-tumor effect. A subject may continue nutritional therapy until the cancer shows at least a partial, or more preferably, a complete response. In certain embodiments, the subject may continue nutritional therapy for at least 1 month to 3 months, at least 1 month to 4 months, at least 5 months to 1 year, including any period of time within these ranges, such as 1 month, 2 months, 2.5 months, 3 months, 3.5 months, 4 months, 5 months, 6 months, 7 months, 8 months, 9 months, 10 months, 11 months, 1 year, or however long is beneficial for treating the cancer in the subject. Continued nutritional therapy may also be beneficial for preventing recurrence of a cancer or prolonging periods of remission.

In another embodiment, the method further comprises monitoring levels (e.g., in the bloodstream or intracellularly in cancer cells) of one or more nutrients needed for growth of the cancerous cells in the subject. Levels of one or more nutrients needed for growth of the cancerous cells may be monitored for a period during the time the subject is kept on a diet that reduces or eliminates the subject's daily intake of the one or more nutrients needed for growth of the cancerous cells.

In certain embodiments, the diet of the subject is adjusted to reduce the levels of one or more nutrients needed for growth of the cancerous cells to less than 1-10% of the levels (e.g., in the bloodstream or intracellularly in cancer cells) in the subject prior to putting the subject on the diet, including any percentage within this range such as less than 1, 2, 3, 4, 5, 6, 7, 8, 9, or 10%. In one embodiment, the method comprises monitoring levels of at least one amino acid needed for growth of the cancerous cells in blood of the subject.

In another embodiment, the method further comprises monitoring growth of the cancer in the subject during nutritional therapy. Growth of the cancer in the subject may be monitored for a period during the time the subject is kept on a diet that reduces or eliminates the subject's daily intake of the one or more nutrients needed for growth of the cancer. In certain embodiments, the monitoring is used to adjust the diet of the subject to reduce the levels of the one or more nutrients sufficiently to suppress growth of the cancerous cells.

In certain embodiments, a subject is treated for a cancer that has a nutritional weakness making cancer growth and proliferation dependent on at least one amino acid selected from the group consisting of cysteine, arginine, glutamine, serine, and tyrosine.

In certain embodiments, the invention includes a method for treating a subject for a cysteine-dependent cancer comprising putting the subject on a low-cysteine diet that reduces or eliminates the subject's daily intake of foods containing cysteine. Cysteine can be reduced in the diet, for example, by reducing or eliminating the subject's daily intake of cysteine-containing proteins, particularly cysteine-containing animal proteins. In particular, intake of foods typically high in cysteine content, such as, but not limited to, poultry, pork, dairy products, eggs, or grains should be lowered or eliminated. In addition, the subject's daily intake of methionine may be augmented to sustain demands for sulfur-containing amino acids by normal cells. Preferably, the low-cysteine diet provides other nutrients at levels in accordance with United States Recommended Daily Allowances (USRDA) guidelines.

Nutritional therapy may be implemented by providing the subject being treated for cancer with dietary instructions on lowering the amount of cysteine consumed daily. Alternatively, the subject may be provided with low cysteine or cysteine-free meals (e.g., breakfast meals, lunch meals, dinner meals, or snacks having cysteine-free or low-cysteine-containing food) to help the subject comply with the needed dietary restrictions.

In certain embodiments, the low-cysteine diet reduces the subject's daily intake of foods containing cysteine by at least 70% to 100%, including any percent within this range, such as 70, 75, 80, 85, 90, 91, 92, 93, 94, 95, 96, 97, 98, 99, or 100%. The low-cysteine diet should reduce the subject's daily intake of cysteine in any form, including oxidized cysteine derivatives such as cystine.

In another embodiment, the subject is put on a protein-free diet and further administered an amino acid-containing supplement comprising all of the essential amino acids (i.e., histidine, isoleucine, leucine, lysine, methionine, phenylalanine, threonine, tryptophan, and valine). The amino acid-containing supplement may further comprise one or more nonessential amino acids selected from the group consisting of alanine, arginine, asparagine, aspartate, glutamate, glutamine, glycine, proline, serine, and tyrosine, provided that the amino acid-containing supplement does not contain cysteine or cystine.

The methods of the invention can be used for treating a subject for any cancer that is responsive to a low-cysteine diet, for example, adenocarcinoma, squamous cell carcinoma, large cell carcinoma, or small cell carcinoma. In certain embodiments, the cancer is lung cancer (e.g., squamous cell lung carcinoma, large cell lung carcinoma, or small cell lung carcinoma), liver cancer, breast cancer, prostate cancer, colon cancer, lymphoma, or leukemia.

The subject may be treated either therapeutically for an existing cysteine-dependent cancer or prophylactically (e.g., a subject at risk of developing cancer because of a genetic predisposition or presence of one or more developmental, environmental, occupational, or behavioral risk factors). In particular, a subject may be treated prophylactically if the subject is at risk of having cancer because of smoking, chronic catheterization, or an environmental exposure to a carcinogen. For example, a subject at risk of developing cancer (e.g., having one or more risk factors) may be treated prophylactically for cancer by putting the subject on a low-cysteine diet for 1-3 months. Prophylactic treatment may be repeated, for example, annually, every two years, every three years, every four years, or every five years to reduce the risk of the subject developing cancer or having a recurrence.

In certain embodiments, the method further comprises reducing the subject's daily intake of one or more other amino acids that suppress or prevent proliferation of cancerous cells or tumor growth in the subject due to other nutritional weaknesses of the cancer. In certain embodiments, intake of at least one amino acid selected from the group consisting of arginine, glutamine, serine, and tyrosine is reduced or eliminated in the subject's daily diet.

In certain embodiments, nutritional therapy for treatment of cancer is combined with administration of one or more therapeutic agents or medications that further reduce cysteine or cystine levels (e.g., in the bloodstream or intracellularly in cancer cells) in a subject, such as, but not limited to, a cytsteine/cystine-depleting drug, a cysteine degradation enzyme, a gamma-glutamyl transpeptidase inhibitor, a cysteine/cystine transporter inhibitor, and an inhibitor of cysteine biosynthesis (e.g., inhibitor of cystathionine gamma-lyase inhibitors or cystathionine beta-synthase).

In another embodiment, the method further comprises monitoring levels (e.g., in bloodstream) of cysteine or cystine in the subject. Levels of cysteine or cystine may be monitored for a period during the time the subject is kept on the low-cysteine diet. In certain embodiments, the diet of the subject is adjusted to reduce the levels of cysteine or cystine by 70-100% of the levels in the subject prior to putting the subject on the low-cysteine diet, including any percentage within this range such as 70, 75, 80, 85, 90, 91, 92, 93, 94, 95, 96, 97, 98, 99, or 100%. In one embodiment, the method comprises monitoring levels of cysteine or cystine in blood of the subject.

In another embodiment, the method further comprises monitoring growth of the cancer in the subject. Growth of the cancer in the subject may be monitored for a period during the time the subject is kept on the low-cysteine diet. In certain embodiments, the monitoring is used to adjust the diet of the subject to reduce the levels of cysteine or cystine sufficiently to suppress growth of the cancerous cells.

In certain embodiments, nutritional therapy comprises increasing or decreasing daily intake of one or more vitamins to suppress cancer growth in a subject. In one embodiment, the method comprises administering an effective amount of a multivitamin at a dosage sufficient to reduce growth of a cancer. In another embodiment, the method comprises administering an effective amount of vitamin B2 at a dosage sufficient to reduce growth of a cancer. See, e.g., Example 1 and Table 5 for exemplary cancers exhibiting growth suppression by administration of a multivitamin supplement or vitamin B2. An exemplary multivitamin supplement comprises biotin (B7), choline, calcium pantothenate (B5), folic acid (B9), niacinamide (B3), para-aminobenzoic acid, pyridoxine (B6), riboflavin (B2), thiamine (B1), cobalamin (B12), and i-inositol. In a further embodiment, the method comprises reducing daily intake of vitamin B1 to reduce growth of breast cancer or colon cancer. Such vitamin nutritional therapy (i.e., using control of daily intake of one or more vitamins) can be used alone or in combination with other nutritional therapy, as described herein, such as reducing or eliminating daily intake of one or more nutrients (e.g., nonessential amino acids) needed for growth of a cancer.

In another aspect, the invention includes a prepackaged therapeutic meal for consumption by a subject having a diet-responsive cancer comprising cysteine-free food or low cysteine-containing food. The prepackaged therapeutic meal may be a breakfast meal, a lunch meal, a dinner meal, or a snack. In one embodiment, the prepackaged therapeutic meal is a protein-free meal comprising an amino acid-containing supplement comprising all of the essential amino acids (i.e., histidine, isoleucine, leucine, lysine, methionine, phenylalanine, threonine, tryptophan, and valine). The amino acid-containing supplement may further comprise one or more nonessential amino acids selected from the group consisting of alanine, arginine, asparagine, aspartate, glutamate, glutamine, glycine, proline, serine, and tyrosine, provided that the amino acid-containing supplement does not contain cysteine or cystine.

The methods of the invention may be combined with any other method of treating cancer, such as, but not limited to, surgery, radiation therapy, chemotherapy, hormonal therapy, immunotherapy, or biologic therapy.

In yet another aspect, the invention provides kits for use in screening cancerous cells for a nutritional weakness. The kit may include a plurality of different growth media for culturing cancerous cells, wherein each medium is deficient in at least one nonessential nutrient. In certain embodiments, the kit includes a plurality of different growth media for culturing cancerous cells, wherein each medium is deficient in at least one amino acid selected from the group consisting of cysteine, arginine, glutamine, serine, and tyrosine. In one embodiment, the kit comprises a first medium lacking cysteine, a second medium lacking arginine, a third medium lacking glutamine, a fourth medium lacking serine, and a fifth medium lacking tyrosine. In another embodiment, the kit contains at least one medium deficient in at least 2, or at least 3, or at least 4, or all of the cysteine, arginine, glutamine, serine, and tyrosine amino acids. The different media may be packaged in separate containers. Additionally, the kit may comprise one or more vitamins or a multivitamin supplement (e.g., in media or separate). The kit may further comprise instructions for identifying a nutritional weakness of a cancerous cell, as described herein.

These and other embodiments of the subject invention will readily occur to those of skill in the art in view of the disclosure herein.

BRIEF DESCRIPTION OF THE FIGURES

FIGS. 2E and 2D show the relative growth of normal human peripheral blood mononuclear cells (PBMC) in non-activated (FIG. 2E) and activated states (FIG. 2F) in the same medium panel. The PBMCS were activated with 5 µg/ml phytohemagglutinin (PHA). The vitality of human red blood cells was not impaired by cystine restriction or dropout after two days of treatment. The error bars are standard errors of the mean of five technical replicates each.

Figure 7A:
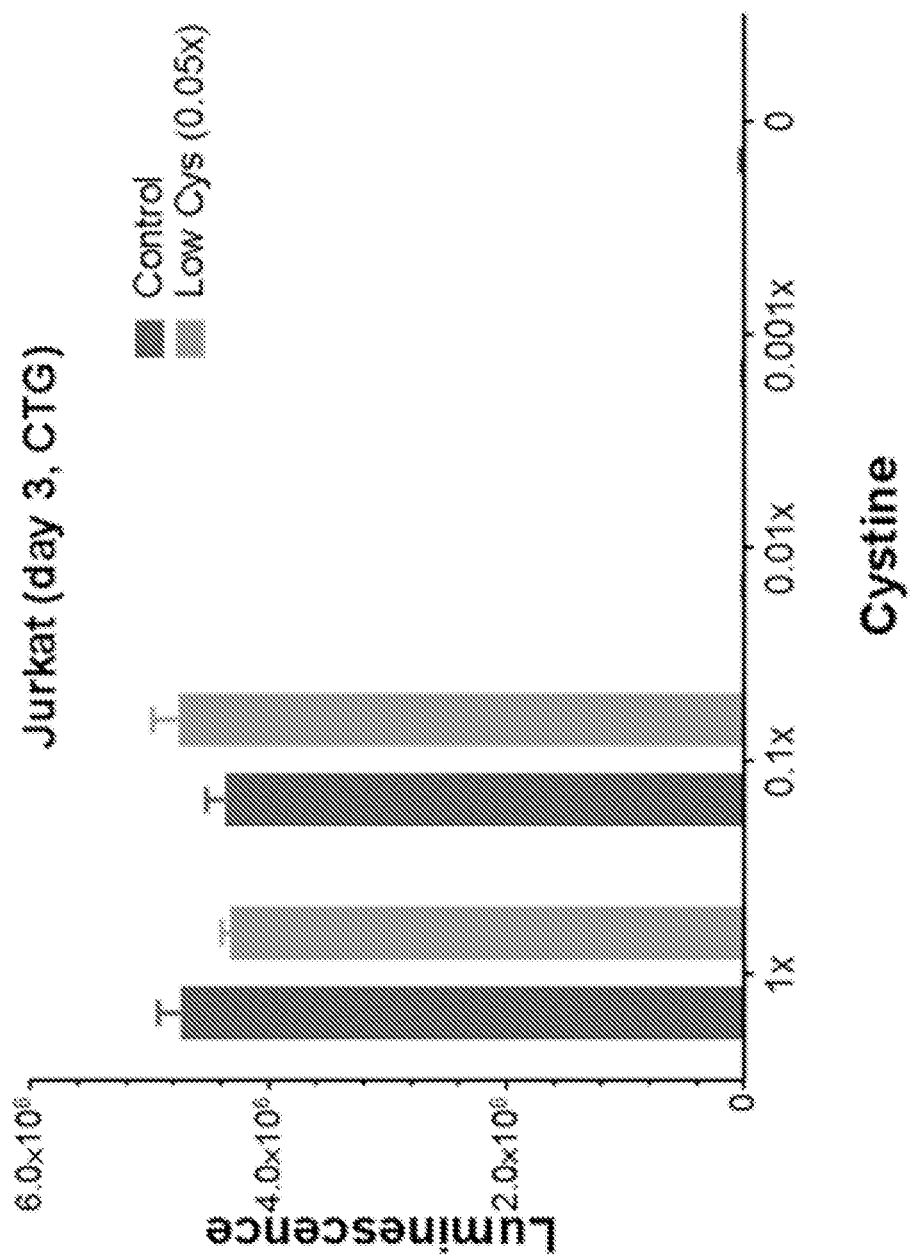
FIGS. 7A-7D show the lack of tolerance to cystine dropout of cells pre-treated with low cystine. Before performing the growth assay, Jurkat (FIG. 7A), HL60 (FIG.
Figure 7B:
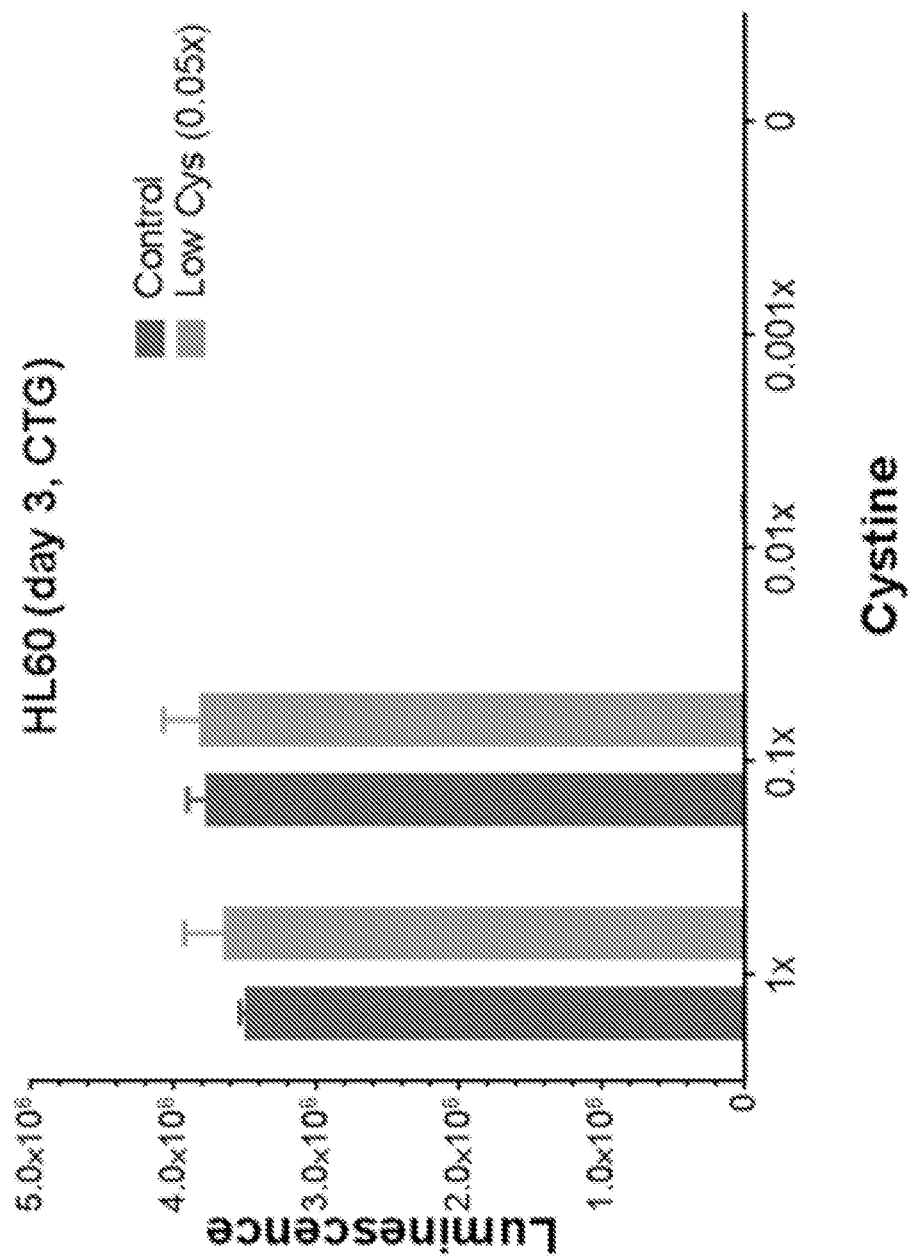
Figure 7C:
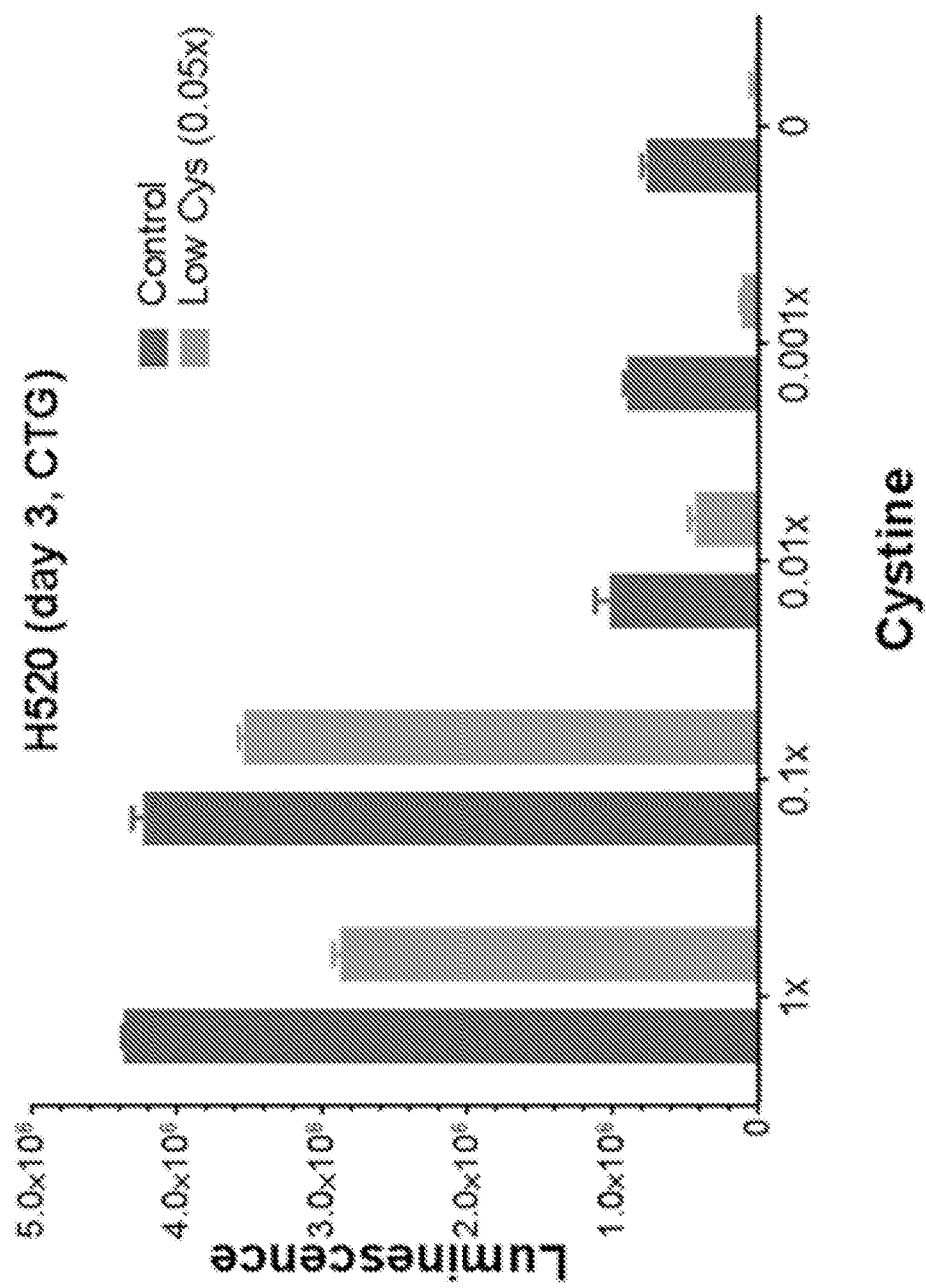
Figure 7D:
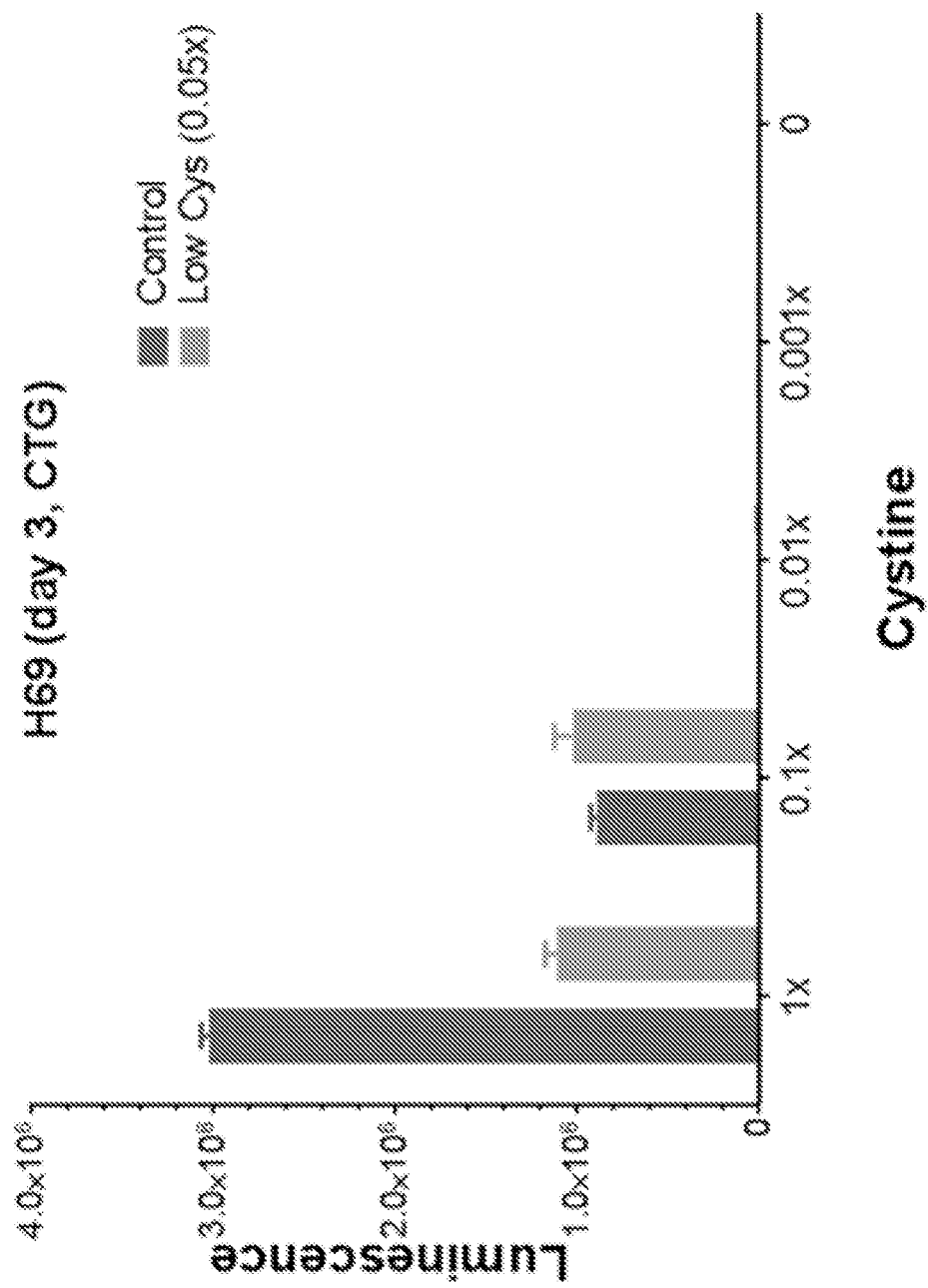

7B), H520 (FIG. 7C), and H69 (FIG. 7D) cells were pretreated with normal (1×, control, dark gray) or low cystine (0.05×, light gray) media for 6 months.

Figure 8A:
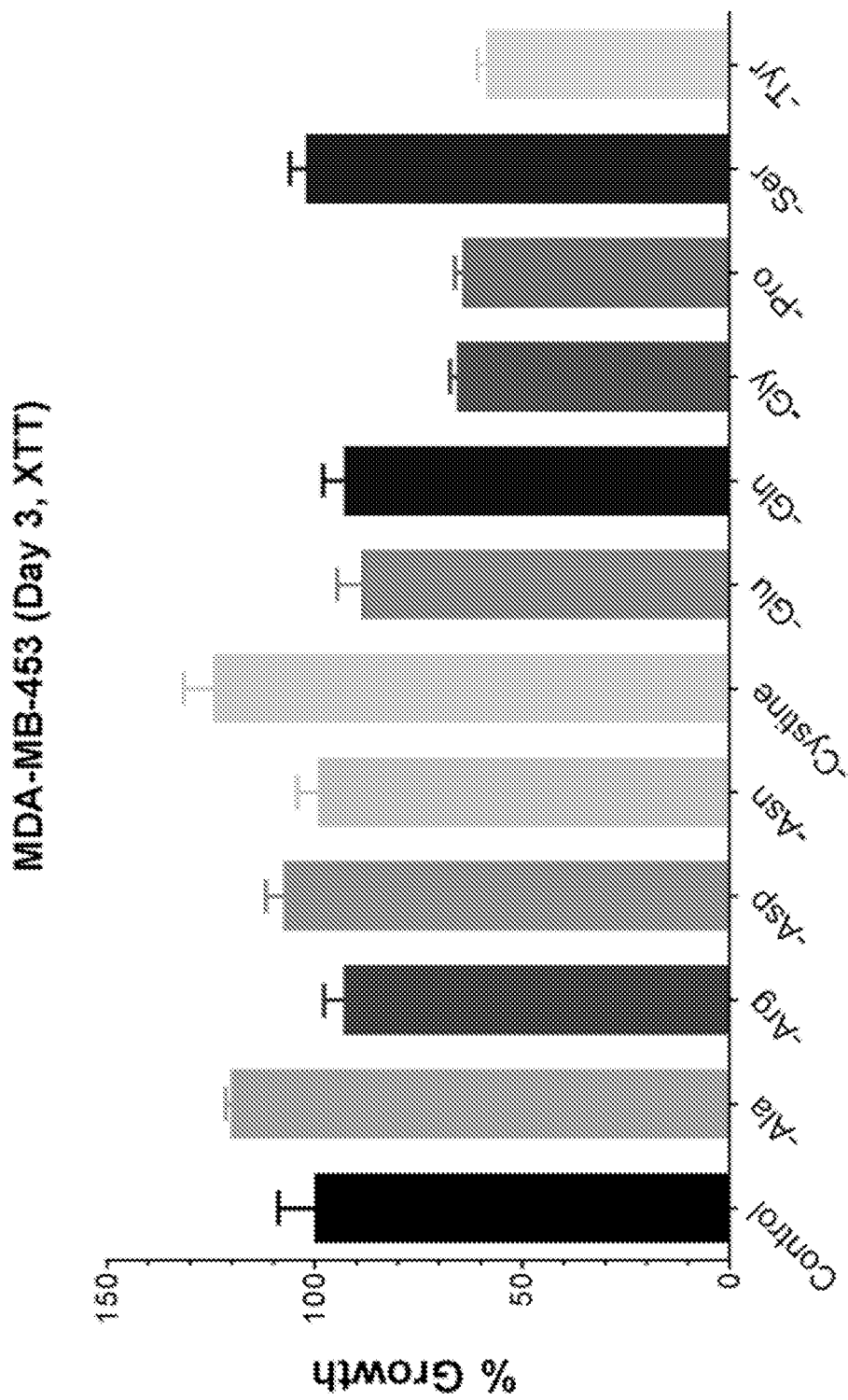
Figure 8B:
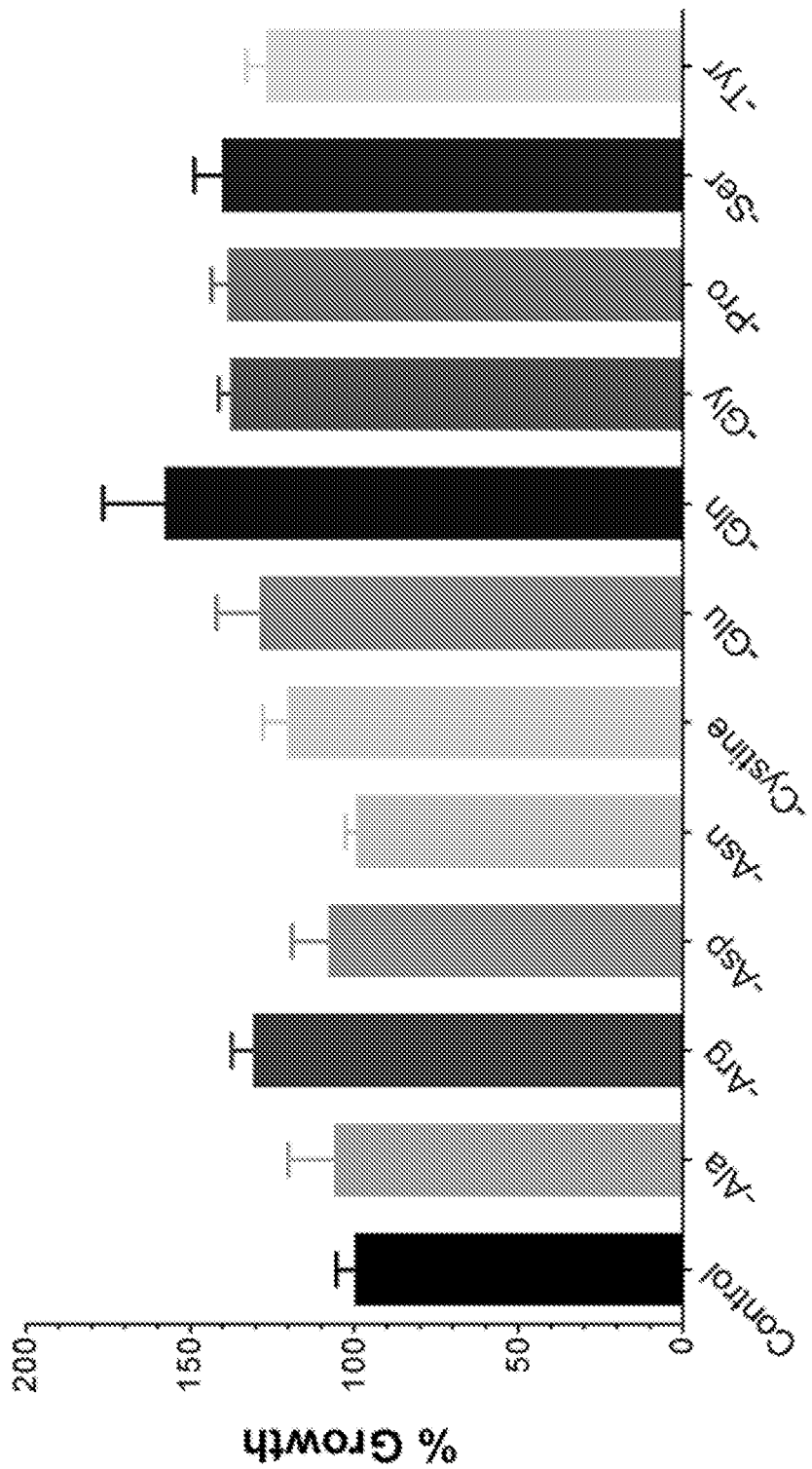
Figure 8C:
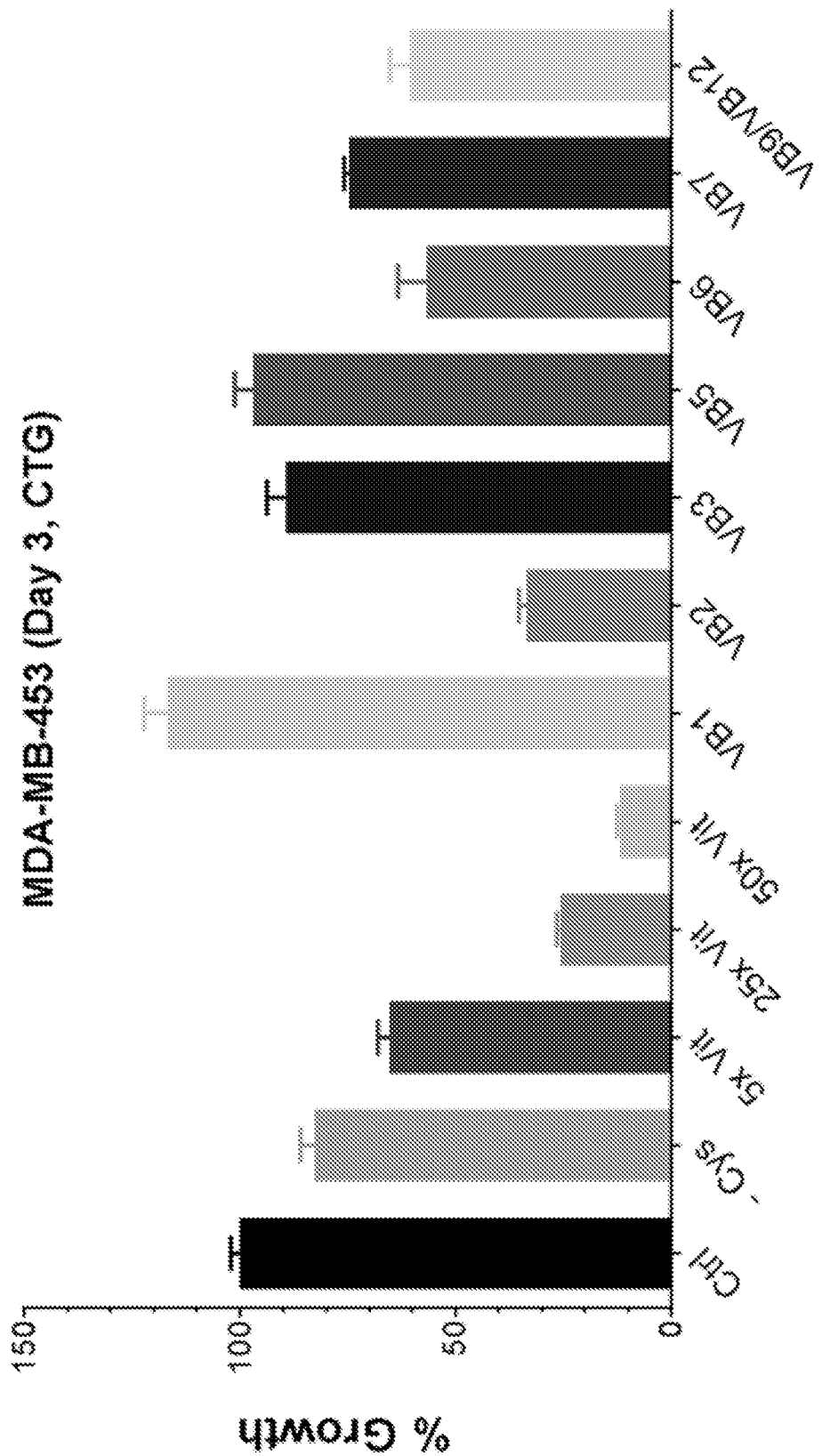

FIGS. 8A-8C show the tolerance to cystine dropout of a non-tumorigenic cell line. The breast cancer cell line, MDA-MB-453, exhibited no sensitivity to cystine dropout (FIGS. 8A and 8B). However, growth of MDA-MB-453 was suppressed by treatment with vitamin supplements (FIG. 8C). In FIG. 8C, all treatments other than the control contained no cysteine. Cells were supplemented with 50× amounts of the individual vitamins if the amount is not already indicated on the graph. Vit contains all vitamins.

DETAILED DESCRIPTION

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., T. Seyfried *Cancer as a Metabolic Disease: On the Origin, Management, and Prevention of Cancer* (Wiley, 2012); *Tumor Cell Metabolism: Pathways, Regulation and Biology* (S. Mazurek and M. Shoshan eds., Springer, 2015); *Cancer Cell Lines (Human Cell Culture)* $1999^{th}$ Edition (J. Masters and B. Palsson eds., Springer, 2013); P. C. Nasca and H. Pastides *Fundamentals Of Cancer Epidemiology* (Jones & Bartlett Publishing Co., $2^{nd}$ edition, 2007); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a cancer cell" includes a mixture of two or more cancer cells, and the like.

The term "about," particularly in reference to a given quantity, is meant to encompass deviations of plus or minus five percent.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, prostate cancer, lung cancer, ovarian cancer, testicular cancer, colon cancer, pancreatic cancer, gastric cancer, hepatic cancer, leukemia, lymphoma, myeloma, adrenal cancer, thyroid cancer, pituitary cancer, renal cancer, brain cancer, skin cancer, head cancer, neck cancer, oral cavity cancer, tongue cancer, and throat cancer.

By "anti-tumor effect" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

The term "tumor response" as used herein means a reduction or elimination of all measurable lesions. The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response" (CR) as used herein means a complete disappearance of all clinically detectable malignant disease, determined by 2 assessments at least 4 weeks apart.

The term "partial response" (PR) as used herein means a 50% or greater reduction from baseline in the sum of the products of the longest perpendicular diameters of all measurable disease without progression of evaluable disease and without evidence of any new lesions as determined by at least two consecutive assessments at least four weeks apart. Assessments should show a partial decrease in the size of lytic lesions, recalcifications of lytic lesions, or decreased density of blastic lesions.

The terms "subject," "individual" or "patient" are used interchangeably herein and refer to a vertebrate, preferably a mammal. By "vertebrate" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue, cells, or fluid isolated from a subject, including but not limited to, for example, urine, blood, plasma, serum, fecal matter, bone marrow, bile, spinal fluid, lymph fluid, samples of the skin, external secretions of the skin, respiratory, intestinal, and genitourinary tracts, tears, saliva, milk, blood cells, organs, biopsies, and also samples containing cells or tissues derived from the subject and grown in culture, and in vitro cell culture constituents, including but not limited to, conditioned media resulting from the growth of cells and tissues in culture, recombinant cells, cancerous cells, and cell components.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention relates to a systematic method for screening cancerous cells to identify nutritional weaknesses and methods of treating cancer by using nutritional therapy to suppress cancer growth. Certain cancers depend on being supplied with one or more nutrients that are nonessential for normal cells. The inventors have developed a screening method in which cancerous cells are grown in culture on media lacking particular nutrients in order to identify nutrients whose absence leads to reduced cancer cell growth and proliferation, or even cell death (see Example 1). This method of screening for nutritional weaknesses is applicable to any laboratory cancer cell lines or culturable clinical tumor cells (see Example 1). Once a nutritional weakness is identified for a particular type of cancer, a subject can be treated for that cancer nutritionally by putting the subject on a restricted diet that deprives cancerous cells of one or more nutrients needed for cancer proliferation and growth.

In order to further an understanding of the invention, a more detailed discussion is provided below regarding methods of screening cancerous cells for nutritional weaknesses and methods of exploiting the identified weaknesses to treat cancer nutritionally.

A. Screening Cancerous Cells for Nutritional Weaknesses

Nutritional weaknesses can be identified in cancerous cells by culturing cancerous cells in media having all essential nutrients for growth of a normal cell, but lacking at least one nutrient that is nonessential for growth of the normal cell, but needed for growth of the cancerous cells. Suppression of growth of cancerous cells in media lacking at least one nutrient that is nonessential for growth of a normal cell indicates that the cancerous cells have a nutritional weakness, that is, the cancerous cells are dependent on at least one nutrient that is nonessential for growth of normal cells. This method can be used to identify diet-responsive cancers, wherein depriving the cancer of one or more nutrients identified by screening as described herein, suppresses growth and proliferation of the cancer, or more preferably, induces cell death.

The cancerous cells to be screened for nutritional weaknesses may be obtained, for example, from any cancer cell line. In certain embodiments, the cancer cell line is a vertebrate cell line, preferably a mammalian cell line, and more preferably, a human cancer cell line. For a description of various cancer cell lines that are available and genetic mutations associated with various types of cancer, see, e.g., The Cancer Cell Line Encyclopedia (CCLE) project (broadinstitute.org/software/cprg/?q=node/11) and Wellcome Trust Sanger Institute: Cancer Genome. Project and the COSMIC database (cancer.sanger.ac.uk/cell_lines). See also Gazdar et al. (2010) J. Natl. Cancer Inst. 102(17):1310-1321 and Linnoila (1996) J. Cell Biochem. Suppl. 24:92-106 for a description of lung cancer cell lines, Drexler et al. (1998) Leuk. Lymphoma 31(3-4):305-316, Drexler et al. (2004) Leukemia 18(2):227-232, Matsuo (1998) Leuk. Res. 22(7): 567-579, Tohyama et al. (1997) Int. J. Hematol. 65(4):309-317, and Drexler et al. (1995) Leuk. Res. 19(10):681-691 for a description of leukemia and lymphoma cell lines, Neve et al. (2006) Cancer Cell. 10(6):515-527 and Osborne et al. (1987) Breast Cancer Res Treat. 9(2): 111-121 for a description of breast cancer cell lines, Mouradov et al. (2014) Cancer Res. 74(12):3238-3247 for a description of colorectal cancer cell lines, Sobel et al. (2005) J. Urol. 173(2):342-359 for a description of prostate cancer cell lines, Saiselet et al. Front Endocrinol (2012) 3:133 for a description of thyroid cancer cell lines, and Klijn et al. (2015) Nat. Biotechnol. 33(3):306-312 and Cancer Cell Lines (Human Cell Culture) 1999$^{th}$ Edition (J. Masters and B. Palsson eds., Springer, 2013) for a description of various human cancer cell lines; herein incorporated by reference in their entireties.

Additionally, cancerous cells and tissue are available from the American Type Culture Collection (ATCC). Exemplary cell lines that may be used in screening for nutritional weaknesses include lung cancer (ATCC No. CRL-11350, TCP-1016, TCP-2030, TCP-2040, CRL-5878, CRL-5944, CRL-5892, CRL-5885, CRL-5908, CRL-5883, CRL-5939, CRL-5914), leukemia (ATCC No. TCP-1010, CRL-2724, CCL-243, CCL-246, CRL-2256, CRL-1929, TIB-153), lymphoma (ATCC No. TCP-1025, TCP-1015, CRL-3006, CRL-2961, CRL-2956, HTB-62, CRL-1593, TIB-162, CRL-2277, CRL-1942, HTB-176), myeloma (ATCC No. CCL-155), breast cancer (ATCC No. 30-4500K, TCP-1001, TCP-2010, CRL-2324). colon and rectal cancer (ATCC No. TCP-1007, TCP-2020, TCP-1006, HTB-38, CCL-235, HTB-39, CCL-227, CCL-253, CCL-231, CRL-2134), bone cancer (ATCC No. TCP-1009), ovarian cancer (ATCC No. TCP-1021, HTB-78), pancreatic cancer (ATCC No. TCP-2060, TCP-1026, CRL-1687), uterine cancer (ATCC No. TCP-1023, CRL-1976, CRL-1671), prostate cancer (ATCC No. PTA-3568), melanoma (ATCC No. TCP-1013, TCP-1014, CRL-11147, HTB-71, CRL-7898, HTB-63, HTB-69, CRL-1424, HTB-68), stomach cancer (ATCC No. TCP-1008, CRL-5974, CRL-5973, CRL-5971), brain cancer (ATCC No. TCP-1017, CRL-1620, HTB-14, HTB-12, CRL-2273), liver cancer (ATCC No. TCP-1011, HTB-52), bladder cancer (ATCC No. TCP-1020, CRL-1473), epithelial cancer (ATCC No. CCL-255, HTB-26), liposarcoma (ATCC No. HTB-92), muscle cancer (ATCC No. CRL-1598, CCL-136), synovial cancer (ATCC No. HTB-93), glial cell cancer (CRL-2020), and tongue cancer (ATCC No. CRL-1624) cell lines.

Alternatively, the cancerous cells can be obtained from a biological sample from a subject who has cancer. The biological sample is typically a biopsy of abnormal tissue suspected of containing cancerous cells or a bodily fluid such as blood or urine containing cancerous cells. The biological sample may also include samples from in vitro cell culture resulting from the growth of cells, tissues, or organs in culture. The biological sample can be obtained from the subject by conventional techniques. For example, samples of tissue or cells can be obtained by surgical techniques, blood can be obtained by venipuncture, and urine can be spontaneously voided by a subject or collected by bladder catheterization using methods well known in the art.

In certain embodiments, the biological sample may comprise a tissue sample including a portion, piece, part, segment, or fraction of a tissue which is obtained or removed from an intact tissue of a subject. Tissue samples can be obtained, for example, from the breast, pancreas, stomach, liver, secretory gland, bladder, lung, prostate gland, ovary, cervix, uterus, brain, eye, connective tissue, bone, muscles, vasculature, skin, oral cavity, tongue, head, neck, or throat. A tissue biopsy may be obtained by methods including, but not limited to, an aspiration biopsy, a brush biopsy, a surface biopsy, a needle biopsy, a punch biopsy, an excision biopsy, an open biopsy, an incision biopsy or an endoscopic biopsy.

In certain embodiments, the biological sample is a tumor sample, including the entire tumor or a portion, piece, part, segment, or fraction of a tumor. A tumor sample can be obtained from a solid tumor or from a non-solid tumor, for example, from a squamous cell carcinoma, skin carcinoma, oral cavity carcinoma, head carcinoma, throat carcinoma, neck carcinoma, breast carcinoma, lung carcinoma, basal cell carcinoma, a colon carcinoma, a cervical carcinoma, Kaposi sarcoma, prostate carcinoma, an adenocarcinoma, a melanoma, hemangioma, meningioma, astrocytoma, neuroblastoma, carcinoma of the pancreas, gastric carcinoma, colorectal carcinoma, colon carcinoma, transitional cell carcinoma of the bladder, carcinoma of the larynx, chronic myeloid leukemia, acute lymphocytic leukemia, acute promyelocytic leukemia, multiple myeloma, T-cell lymphoma, B-cell lymphomas, retinoblastoma, sarcoma gallbladder, or bronchial cancer. The tumor sample may be obtained from a primary tumor or from a metastatic lesion.

Growth of cancerous cells may be compared to that of normal or control cells from a normal biological sample. A "normal" sample as used herein refers to a biological sample, such as tissue or cells that are not diseased. That is, a normal sample is obtained from a normal subject (e.g. an individual known to not have cancer or any condition or symptom associated with abnormal cell maturation or proliferation).

Cancerous cells may be screened, for example, for dependence on nonessential amino acids (i.e., not needed for growth of normal cells). In one embodiment, cancerous cells are screened for dependence on one or more amino acids selected from the group consisting of cysteine, arginine, glutamine, serine, and tyrosine by culturing the cancerous cells on media deficient in at least one of these amino acids and identifying cancerous cells, which have nutritional weaknesses, based on poor growth or cell death in the absence of one or more of these amino acids.

Alternatively or additionally, cancerous cells may be screened for dependence of their growth on vitamins. In one embodiment, cancerous cells are screened for dependence on one or more vitamins selected from the group consisting of biotin (B7), choline, calcium pantothenate (B5), folic acid (B9), niacinamide (B3), para-aminobenzoic acid, pyridoxine (B6), riboflavin (B2), thiamine (B1), cobalamin (B12), and i-inositol. In another embodiment, cancerous cells are screened for the effects of increasing dosage of a multivitamin supplement on growth. An exemplary multivitamin supplement comprises biotin (B7), choline, calcium pantothenate (B5), folic acid (B9), niacinamide (B3), para-aminobenzoic acid, pyridoxine (B6), riboflavin (B2), thiamine (B1), cobalamin (B12), and i-inositol.

B. Kits

In another aspect, the invention provides kits for use in screening cancerous cells for nutritional weaknesses. For example, the kits can be used to identify one or more nutrients that are needed for growth and proliferation of cancer cells, but nonessential to normal cells. The kit may include a plurality of different growth media for culturing cancerous cells, wherein each medium is deficient in at least one nonessential nutrient. In certain embodiments, the kit includes a plurality of different growth media for culturing cancerous cells, wherein each medium is deficient in at least one amino acid selected from the group consisting of cysteine, arginine, glutamine, serine, and tyrosine. The kit may further comprise one or more additional reagents for promoting growth of cancer cells (e.g., growth factors and other media supplements) or control reference samples (e.g., normal cells).

In one embodiment, the kit contains a first medium lacking cysteine, a second medium lacking arginine, a third medium lacking glutamine, a fourth medium lacking serine, and a fifth medium lacking tyrosine.

In certain embodiments, the kit contains at least one medium deficient in more than one nutrient. For example, the kit may contain at least one medium deficient in at least 2, or at least 3, or at least 4, or all of the cysteine, arginine, glutamine, serine, and tyrosine amino acids.

In another embodiment, the kit further comprises one or more vitamins selected from biotin (B7), choline, calcium pantothenate (B5), folic acid (B9), niacinamide (B3), para-aminobenzoic acid, pyridoxine (B6), riboflavin (B2), thiamine (B1), cobalamin (B12), and i-inositol, or any combination thereof for testing growth dependence of cancerous cells on levels of vitamins. Vitamins may be included in the media compositions or separate.

The kit can comprise one or more containers for different media compositions and/or vitamins contained in the kit. The different media and other agents may be packaged in separate containers. Compositions can be in liquid form or can be lyophilized. Suitable containers for the compositions include, for example, bottles, vials, syringes, and test tubes. Containers can be formed from a variety of materials, including glass or plastic. The kit can also comprise a package insert containing written instructions for identifying a nutritional weakness of a cancerous cell, as described herein.

C. Methods of Treating Cancer

Once nutritional weaknesses are identified for a particular type of cancer, a subject having a diet-responsive cancer can be treated for that cancer nutritionally (i.e., nutritional therapy) by putting the subject on a restricted diet that deprives cancerous cells of one or more nutrients needed for cancer growth and proliferation. For example, the restricted diet may reduce the subject's daily intake of foods containing a nutrient needed by cancer cells by at least 70% to 100%, including any percent within this range, such as 70, 75, 80, 85, 90, 91, 92, 93, 94, 95, 96, 97, 98, 99, or 100%.

Nutritional therapy may be implemented by providing the subject being treated for cancer with dietary instructions for reducing or eliminating daily intake of one or more nutrients associated with nutritional weaknesses of a cancer. Alternatively, the subject may be provided with prepackaged therapeutic meals (e.g., breakfast meals, lunch meals, dinner meals, or snacks) that do not contain or have low amounts of one or more nutrients associated with nutritional weaknesses of a cancer. Such prepackaged therapeutic meals may aid patients in complying with dietary restrictions. Preferably, any prescribed diet provides other nutrients at levels in accordance with United States Recommended Daily Allowances (USRDA) guidelines.

In certain embodiments, a subject is treated for a diet-responsive cancer nutritionally by reducing or eliminating daily consumption of one or more amino acids that are nonessential to normal cells, but needed for growth of the cancer for which the individual is undergoing therapy. In this case, the prepackaged therapeutic meal may be a protein-free or low-protein meal comprising an amino acid-containing supplement comprising all of the essential amino acids (i.e., histidine, isoleucine, leucine, lysine, methionine, phenylalanine, threonine, tryptophan, and valine). The amino acid-containing supplement may further comprise one or more nonessential amino acids selected from the group consisting of alanine, arginine, asparagine, aspartate, glutamate, glutamine, glycine, proline, serine, and tyrosine, provided that the amino acid-containing supplement does not contain does not contain any nonessential amino acid identified by the methods described herein as needed for growth of the cancer for which the individual is undergoing therapy.

Nutritional therapy should bring about a positive therapeutic response with respect to treatment of an individual for a particular cancer, such as an anti-tumor effect, as defined herein. By "positive therapeutic response" is intended that the individual undergoing the nutritional therapy according to the invention exhibits an improvement in one or more symptoms of the cancer for which the individual is undergoing therapy. For example, a positive therapeutic response can refer to one or more of the following improvements: (1) reduction in tumor size; (2) reduction in the number of cancer cells; (3) inhibition (i.e., slowing to some extent, preferably halting) of tumor growth; (4) inhibition (i.e., slowing to some extent, preferably halting) of cancer cell infiltration into peripheral organs; (5) inhibition (i.e., slowing to some extent, preferably halting) of tumor metastasis; and (6) some extent of relief from one or more symptoms associated with the cancer (e.g., pain, fatigue).

Such therapeutic responses may be further characterized as to degree of improvement. Thus, for example, an improvement may be characterized as a complete response. By "complete response" is documentation of the disappearance of all symptoms and signs of all measurable or evaluable disease confirmed by physical examination, laboratory, nuclear and radiographic studies (i.e., CT (computer tomography) and/or MRI (magnetic resonance imaging)), and other non-invasive procedures repeated for all initial abnormalities or sites positive at the time of entry into the study. Alternatively, an improvement in the cancer may be categorized as being a partial response. By "partial response" is intended a reduction of greater than 50% in the sum of the products of the perpendicular diameters of all measurable lesions when compared with pretreatment measurements.

A subject may continue nutritional therapy until the cancer shows at least a partial, or more preferably, a complete response. Preferably, nutritional therapy is continued until the cancer is completely eradicated, however long this may take. For example, a subject may continue nutritional therapy for at least 1 month to 3 months, at least 1 month to 4 months, at least 5 months to 1 year, including any period of time within these ranges, such as 1 month, 2 months, 2.5 months, 3 months, 3.5 months, 4 months, 5 months, 6 months, 7 months, 8 months, 9 months, 10 months, 11 months, 1 year, or however long is beneficial for treating the cancer in the subject. Continued nutritional therapy may also be beneficial for preventing recurrence of a cancer or prolonging periods of remission.

As mentioned above, a subject may be treated nutritionally for a cancer by putting the subject on a diet that reduces or eliminates the subject's daily intake of foods containing one or more nonessential amino acids. In certain embodiments, nutritional therapy comprises reducing or eliminating daily consumption of one or more amino acids selected from the group consisting of cysteine, arginine, glutamine, serine, and tyrosine.

The subject may be put on a protein-free or low-protein diet and further administered an amino acid-containing supplement comprising all of the essential amino acids (i.e., histidine, isoleucine, leucine, lysine, methionine, phenylalanine, threonine, tryptophan, and valine). The amino acid-containing supplement may further comprise one or more nonessential amino acids selected from the group consisting of alanine, arginine, asparagine, aspartate, glutamate, glutamine, glycine, proline, serine, and tyrosine, wherein the amino acid-containing supplement does not contain any amino acid identified by the methods described herein as needed for growth of the cancer for which the individual is undergoing therapy.

As shown in Example 1, cysteine deprivation has been successful in suppressing a variety of cancers. Thus, in one embodiment, a subject is treated nutritionally fora cancer by putting the subject on a low-cysteine diet that reduces or eliminates the subject's daily intake of foods containing cysteine. Cysteine can be reduced in the diet, for example, by reducing the subject's daily intake of cysteine-containing proteins, particularly cysteine-containing animal proteins. In particular, intake of foods typically high in cysteine content, such as, but not limited to, poultry, pork, dairy products, eggs, or grains should be lowered or eliminated. In addition, the subject's daily intake of methionine may be augmented to sustain demands for sulfur-containing amino acids by normal cells. In another embodiment, the subject is put on a protein-free or low-protein diet and further administered an amino acid-containing supplement comprising all of the essential amino acids, wherein the amino acid-containing supplement comprises no cysteine or cystine. The amino acid-containing supplement may further comprise one or more nonessential amino acids selected from the group consisting of alanine, arginine, asparagine, aspartate, glutamate, glutamine, glycine, proline; serine, and tyrosine, provided that the amino acid-containing supplement does not contain cysteine or cystine.

In certain embodiments, the low-cysteine diet reduces the subject's daily intake of foods containing cysteine by at least 70% to 100%, including any percent within this range, such as 70, 75, 80, 85, 90, 91, 92, 93, 94, 95, 96, 97, 98, 99, or 100%. The low-cysteine diet should reduce the subject's daily intake of cysteine in any form, including oxidized cysteine derivatives such as cystine.

The subject may be treated either therapeutically for an existing cysteine-dependent cancer or prophylactically (e.g., a subject at risk of developing cancer because of a genetic predisposition or presence of one or more developmental, environmental, occupational, or behavioral risk factors). In particular, a subject may be treated prophylactically if the subject is at risk of having cancer because of smoking, chronic catheterization, or an environmental exposure to a carcinogen. Subjects in certain occupations, such as, but not limited to, veterans, firefighters, chemists, bus drivers, rubber workers, mechanics, leather workers, blacksmiths, machine setters, or hairdressers may also be at higher risk of developing cancer and benefit from prophylactic treatment. For example, a subject at risk of developing cancer (e.g., having one or more risk factors) may be treated prophylactically for cancer by putting the subject on a low-cysteine diet for 1-3 months. Prophylactic treatment may be repeated, for example, annually, every two years, every three years, every four years, or every five years to reduce the risk of the subject developing cancer or having a recurrence.

Alternatively or additionally, nutritional therapy may comprise increasing or decreasing daily intake of one or more vitamins to suppress cancer growth in a subject. In one embodiment, the method comprises administering an effective amount of a multivitamin at a dosage sufficient to reduce growth of a cancer. In another embodiment, the method comprises administering an effective amount of vitamin B2 at a dosage sufficient to reduce growth of a cancer. See, e.g., Example 1 and Table 5 for exemplary cancers exhibiting growth suppression by administration of a multivitamin supplement or vitamin B2. An exemplary multivitamin supplement comprises biotin (B7), choline, calcium pantothenate (B5), folic acid (B9), niacinamide (B3), para-aminobenzoic acid, pyridoxine (B6), riboflavin (B2), thiamine (B1), cobalamin (B12), and i-inositol. In a further embodiment, the method comprises reducing daily intake of vitamin B1 to reduce growth of breast cancer or colon cancer. Such vitamin nutritional therapy (i.e., using control of daily intake of one or more vitamins) can be used alone or in combination with other nutritional therapy, as described herein, such as reducing or eliminating daily intake of one or more nutrients (e.g., nonessential amino acids) needed for growth of a cancer.

The methods of the invention can be used for treating a subject for any diet-responsive cancer. Thus, nutritional therapy, as described herein, can be used to treat, for example, neoplasia, tumors, or cancers, including benign, malignant, metastatic and non-metastatic types, including any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. Furthermore, the methods described herein can be used to treat various types of cancer, including, but not limited to, breast cancer, prostate cancer, lung cancer, ovarian cancer, testicular cancer, colon cancer, pancreatic cancer, gastric cancer, hepatic cancer, leukemia, lymphoma, myeloma, adrenal cancer, thyroid cancer, pituitary cancer, renal cancer, brain cancer, skin cancer, head cancer, neck cancer, oral cavity cancer, tongue cancer, and throat cancer.

Nutritional therapy may be combined with administration of one or more therapeutic agents or medications that reduce cysteine or cystine levels (e.g., in the bloodstream or intracellularly in cancer cells), including, but not limited to, cytsteine/cystine-depleting drugs such as mercaptoethane sulfonate (mesna), ifosfamide, a combination of ifosfamide and mesna; cysteine degradation enzymes such as AECase (Aeglea Biotherapeutics (Austin, Tex.)); gamma-glutamyl transpeptidase inhibitors such as acivicin, OU749, and GGsTop; cysteine/cistin transporter inhibitors such as sulfasalazine, (S)-4-carboxyphenylglycine, isoxazoles, quisqualate, 1-α-aminoadipate, 1-α-aminopimelate, and L-Glu analogues; and inhibitors of cysteine biosynthesis including inhibitors of cystathionine gamma-lyase inhibitors and cystathionine beta-synthase such as β-cyanoalanine, aminooxyacetic acid, propargylglycine, and L-aminoethoxyvinylglycine.

Additionally, nutritional therapy may be combined with any other medical treatment for cancer, such as, but not limited to, surgery, radiation therapy, chemotherapy, hormonal therapy, immunotherapy, or molecularly targeted or biologic therapy. Any combination of these other medical treatment methods with nutritional therapy, as described herein, may be used to effectively treat cancer in a subject. Even in patients already undergoing cancer treatment by other methods, adding nutritional therapy to the treatment regimen may improve patient outcome.

For example, nutritional therapy may be combined with chemotherapy with one or more chemotherapeutic agents such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, Leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

In another example, nutritional therapy may be combined with targeted therapy with one or more small molecule inhibitors or monoclonal antibodies such as, but not limited to, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax and gossypol; PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; small molecule drug conjugates, such as Vintafolide; serine/threonine kinase inhibitors, such as Temsirolimus (Torisel), Everolimus (Afinitor), Vemurafenib (Zelboraf), Trainetinib (Mekinist), and Dabrafenib (Tafinlar); and monoclonal antibodies, such as Rituximab (marketed as MabThera or Rituxan), Trastuzumab (Herceptin), Alemtuzumab, Cetuximab (marketed as Erbitux), Panitumumab, Bevacizumab (marketed as Avastin), and Ipilimumab (Yervoy).

In a further example, nutritional therapy may be combined with immunotherapy, including, but not limited to, using any of the following: a cancer vaccine (e.g., Sipuleucel-T), antibody therapy (e.g., Alemtuzumab, Ipilimumab, Ofatumumab, Nivolumab, Pembrolizumab, or Rituximab), cytokine therapy (e.g., interferons, including type I (IFNα and IFNβ), type II (IFNγ) and type III (IFNλ) and interleukins, including interleukin-2 (IL-2)), adjuvant immunochemotherapy (e.g., polysaccharide-K), adoptive T-cell therapy, and immune checkpoint blockade therapy.

In addition, the levels (e.g., in the bloodstream or intracellularly in cancer cells) of one or more nutrients needed for growth of the cancerous cells may be monitored in the subject. Levels of one or more nutrients needed for growth of the cancerous cells may be monitored for a period during the time the subject is kept on a diet that reduces or eliminates the subject's daily intake of the one or more nutrients needed for growth of the cancerous cells. In certain embodiments, such monitoring is used to adjust the diet of the subject to reduce the levels of one or more nutrients needed for growth of the cancerous cells to less than 1-10% of the levels (e.g., in the bloodstream or intracellularly in cancer cells) in the subject prior to putting the subject on the diet, including any percentage within this range such as less than 1, 2, 3, 4, 5, 6, 7, 8, 9, or 10%. In one embodiment, the method comprises monitoring levels of at least one nonessential amino acid needed for growth of the cancerous cells in blood of the subject.

In another embodiment, the method further comprises monitoring growth of the cancer in the subject during nutritional therapy. Growth of the cancer in the subject may be monitored for a period during the time the subject is kept on a diet that reduces or eliminates the subject's daily intake of the one or more nutrients needed for growth of the cancer or during vitamin nutritional therapy. In certain embodiments, the monitoring is used to adjust the diet of the subject to reduce the levels of the one or more nutrients (e.g., nonessential amino acids) sufficiently to suppress growth of the cancerous cells. In other embodiments, the monitoring is used to adjust the levels (e.g., increase or decrease) of one or more vitamins or a multivitamin supplement to suppress growth of the cancerous cells.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Determining the Nutritional Weaknesses of Cancer Cells

Introduction

We have developed a systematic method to determine the nutritional weaknesses of cancer cells, which is cancer-only dependence on supply of certain nutrients that are not necessary for normal cells. This method, with minor modification, is applicable to any laboratory cancer cell lines and culturable clinical tumor cells.

Experimental Procedure

1, Preparation of Cultured Cancer Cells
  1) Cultivation of Cancer Cell Lines
  To establish the screening assay for the nutritional weakness of cancer cells, 5 human blood cancer cell lines, 4 human lung cancer cell lines, 1 human colon cancer cell line, 1 human liver cancer cell line, 5 human breast cancer cell lines, and 3 human prostate cancer cell lines were used (Table 1). All 19 cell lines were cultured in reconstituted complementary RPM11640 based media R-comp (Table 2) for more than 10 days before screening assays.
  2) Cultivation of Primary Cancer Cells from Patient
  The diagnostic test on primary cancer cells from individual cancer patients' biopsies starts with the enzymatic, chemical, or mechanical treatment of cancer tissue and subsequent cultivation of primary cancer cells in R-comp media supplemented with various growth factors based on the cancer type. This diagnostic is applicable to clinical samples, using procedures for culturing cells from clinical samples that are well established in both research and clinics (Zheng et al. (2011) Acta Pharmacologica Sinica 32(3):385-392, Mitra et al. (2013) Trends Biotechnol. 31(6):347-354; herein incorporated by reference).

3) Preparation and Activation of Human Peripheral Blood Mononuclear Cells (PBMCs).
  Non-activated and phytohemagglutinin (PHA)-activated human PBMCs were used as normal cell controls to test the toxicity of any non-essential nutrient dropout. PBMCs from four health donors were isolated by density centrifugation on a Percoll gradient. After washing 3 times with Earle's Balanced Salt Solution (EBSS), PBMCs were stimulated with or without 5 μg/ml of PHA and assayed for the effect of the nutrient dropout on cell growth in the R-comp based media.

Figure 1:
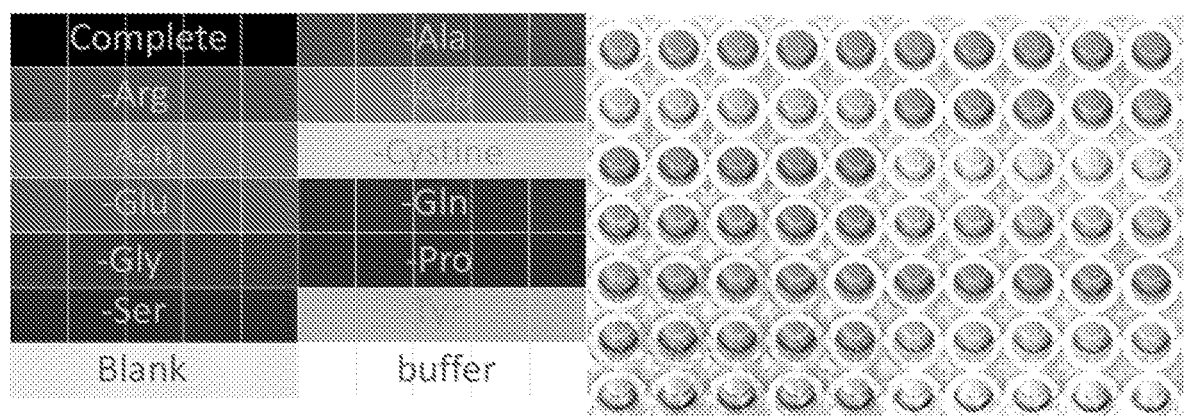
FIG. 1 shows a typical plate layout for the single dropout medium panel. At left is shown the scheme of a plate layout. At right is shown an actual scanned image of an XTT assay of H69 growth over three days. Dark gray indicates cell growth. Blank: Complete medium with no cells. Buffer: phosphate-buffered saline (PBS).
Figure 2A:
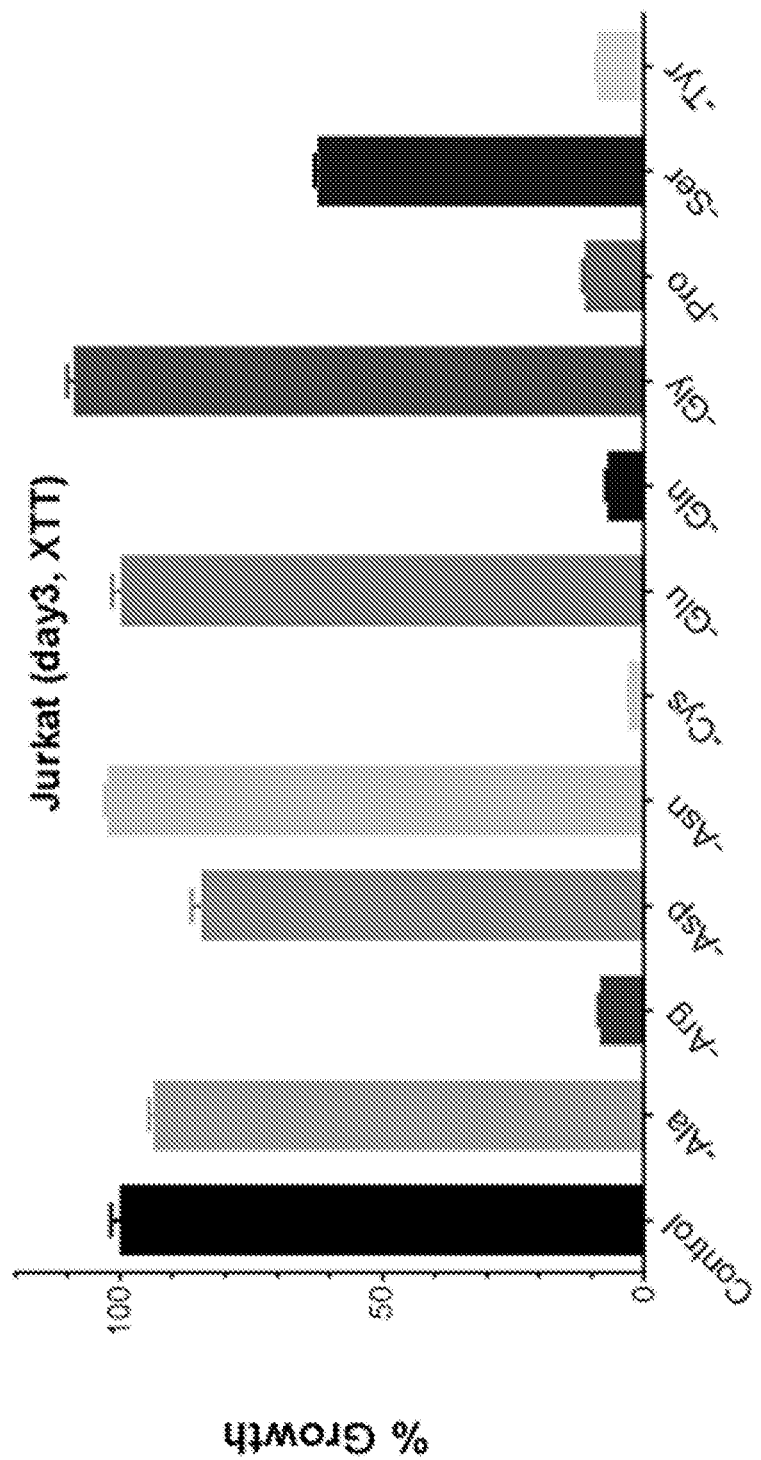
FIGS. 2A-2F show that cancer cells respond differently to medium NEAA dropout. The relative growth of Jurkat (leukemia) and H69 (lung cancer) is plotted from XTT assay (FIGS. 2A and 2B) and CellTiter-Glo assay (CTG, FIGS. 2C and 2D).
Figure 2B:
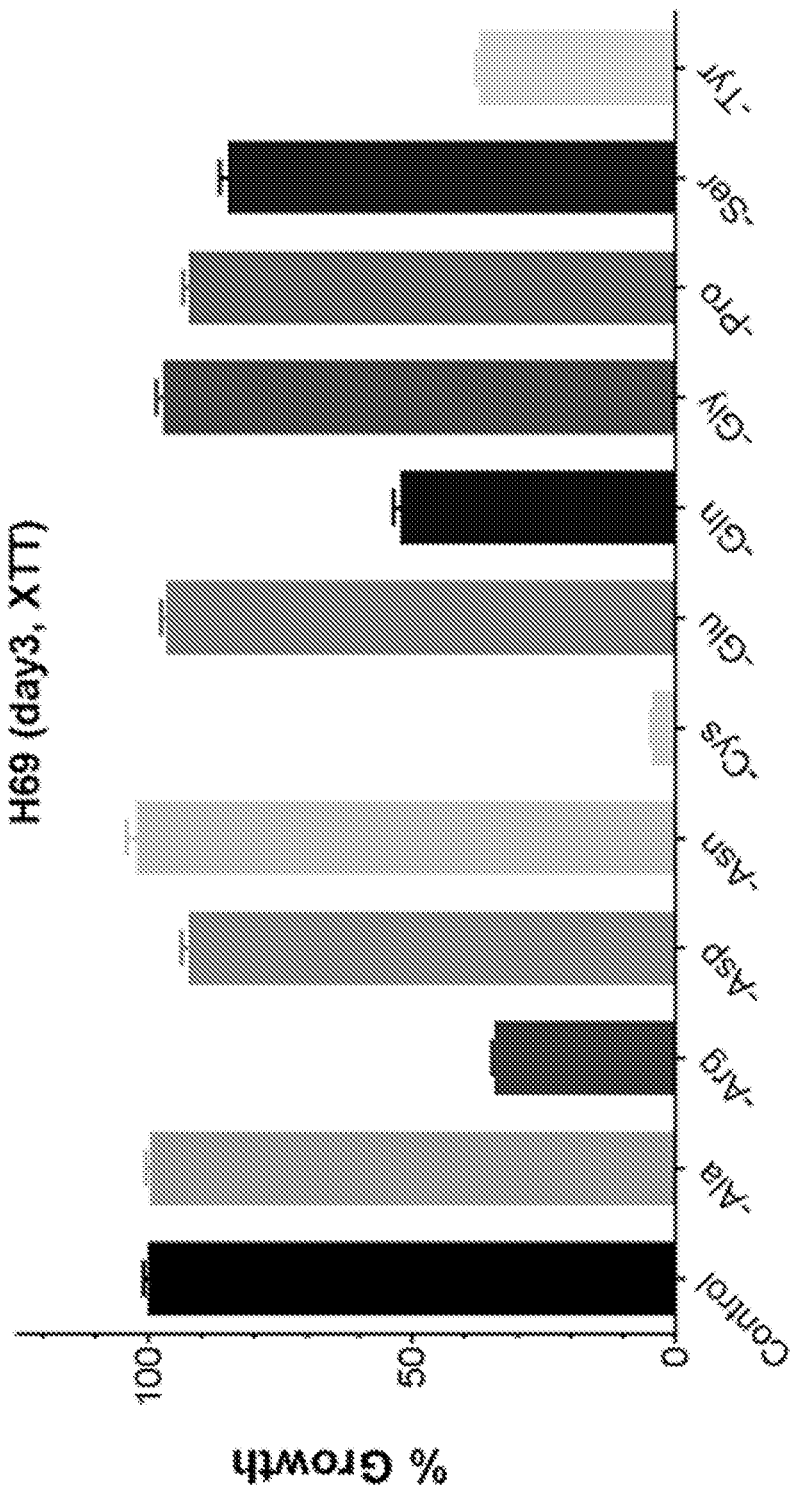
Figure 2C:
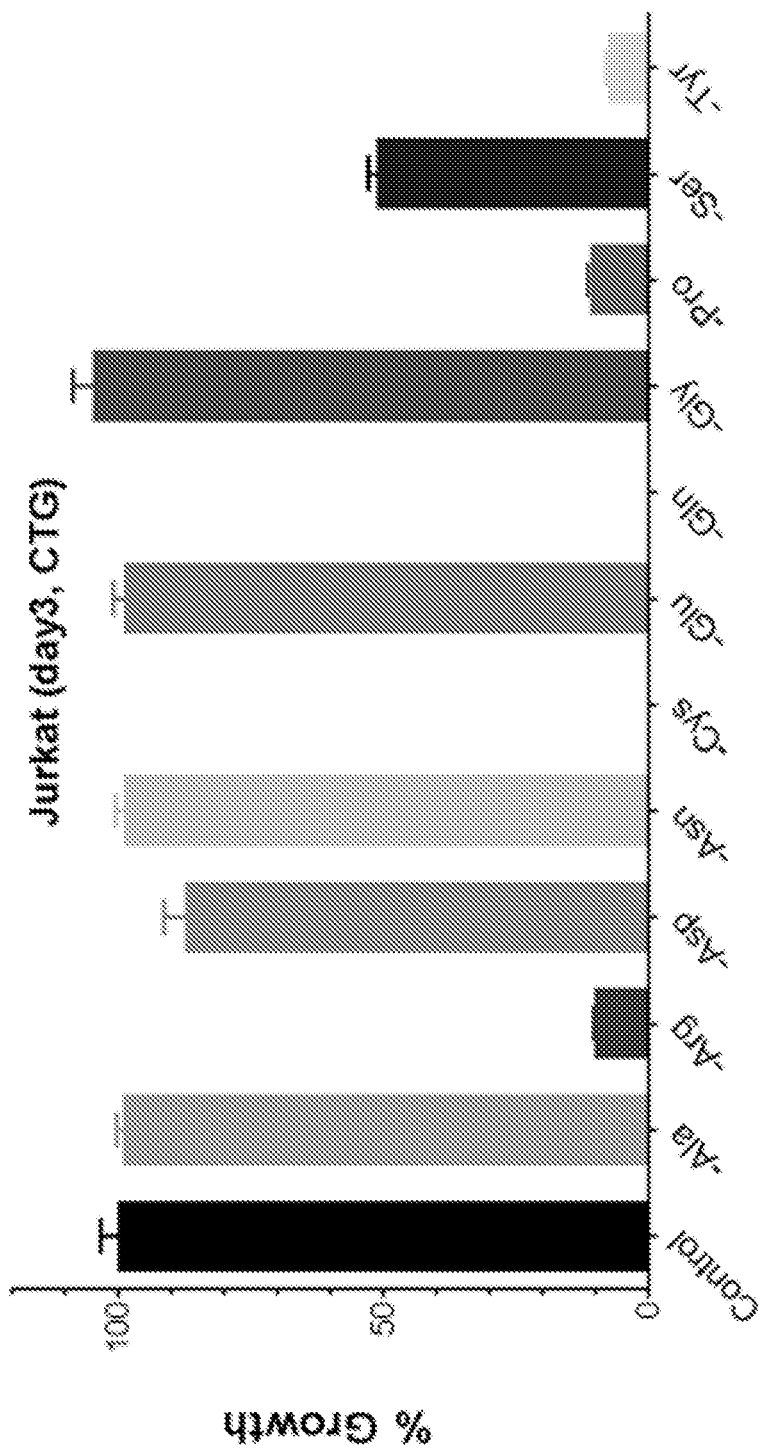
Figure 2D:
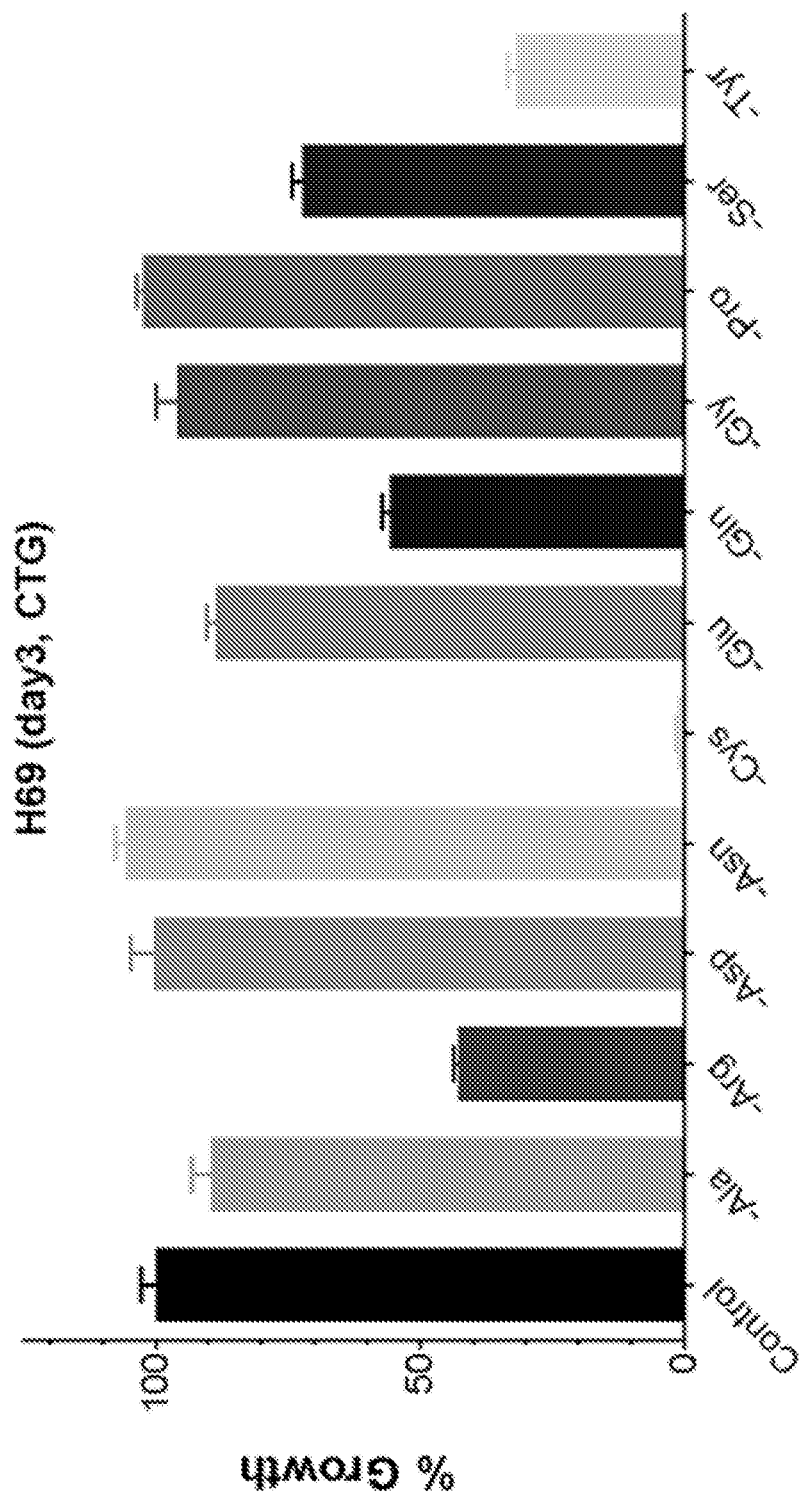
Figure 2E:
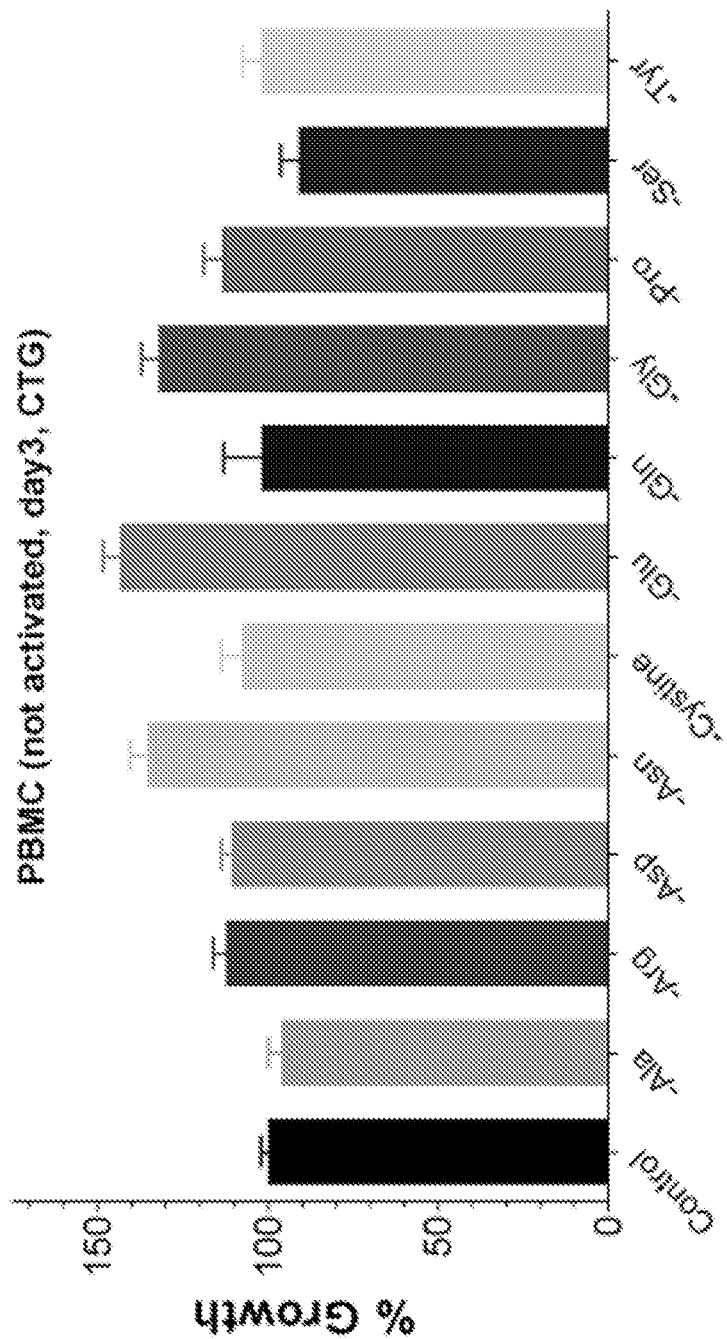
Figure 2F:
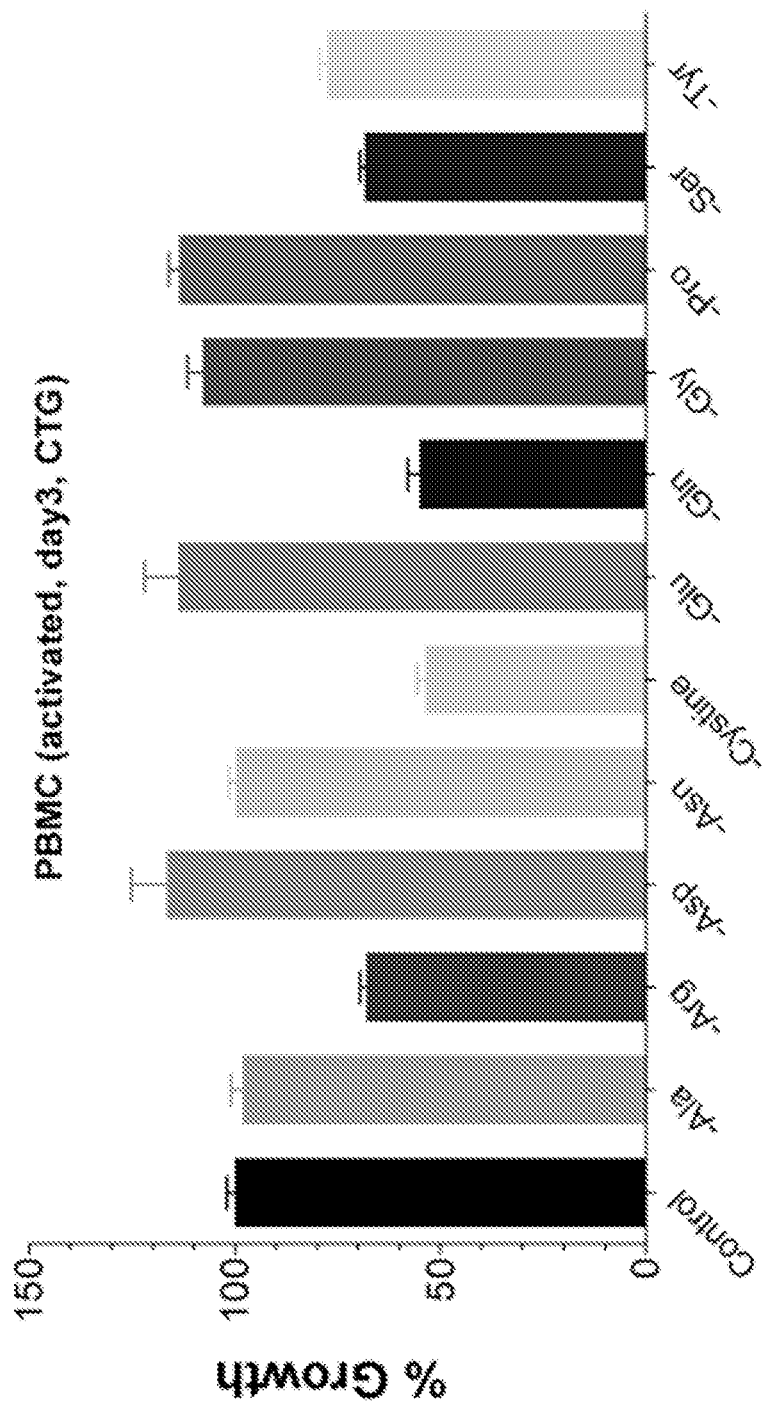
Figure 3A:
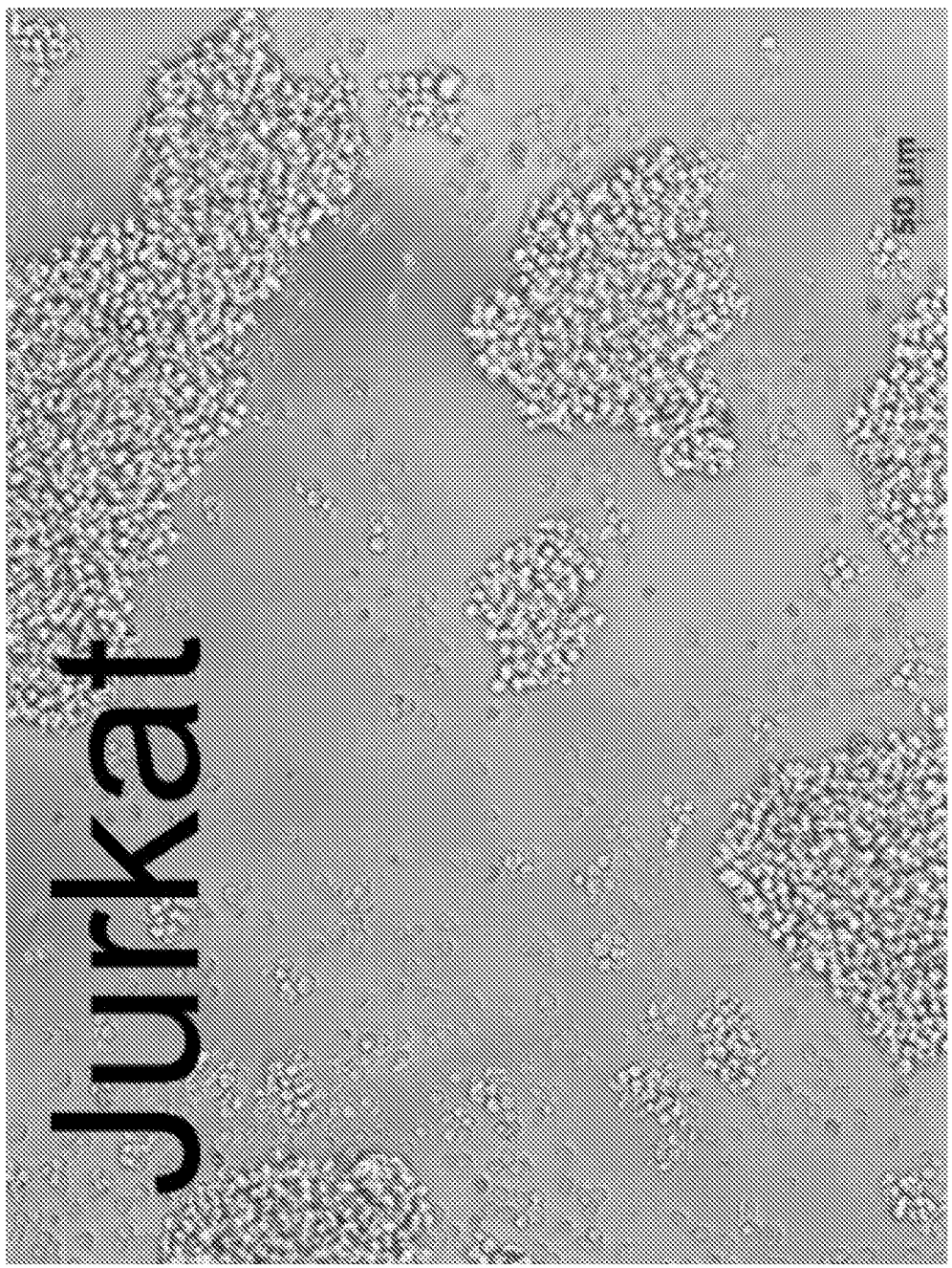
FIGS. 3A-3F show summary of cancer cell morphology. Example pictures of cell morphology are shown for Jurkat (leukemia), H69 and H520 (lung cancer) cells after three days of culture in complete media (FIGS. 3A-3C) or cystine dropout media (FIGS. 3D-3F). Under normal conditions, Jurkat and H69 form clusters in suspension, whereas H520 attaches to a surface to grow. Scale bars are indicated on each graph.
Figure 3B:
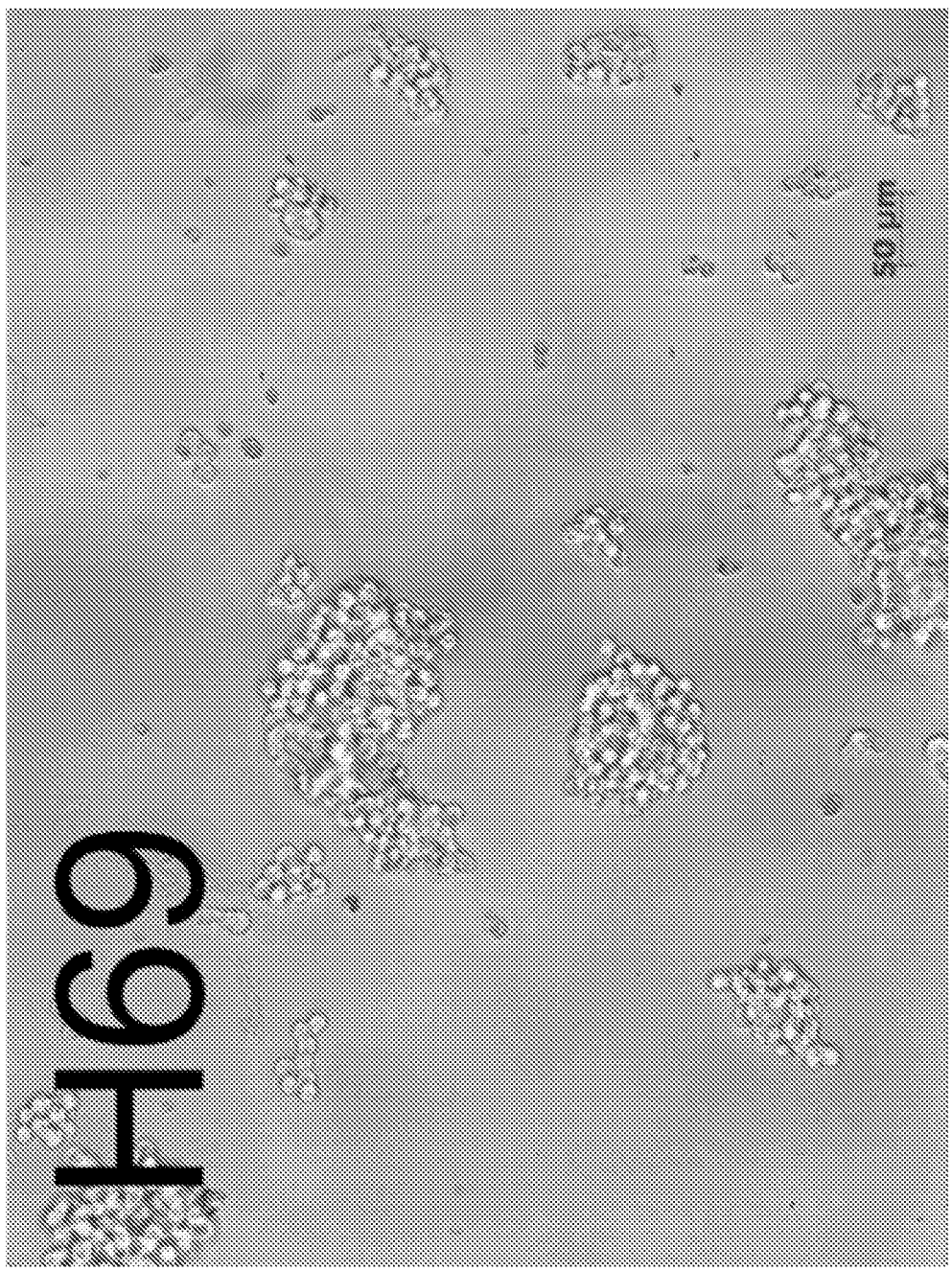
Figure 3C:
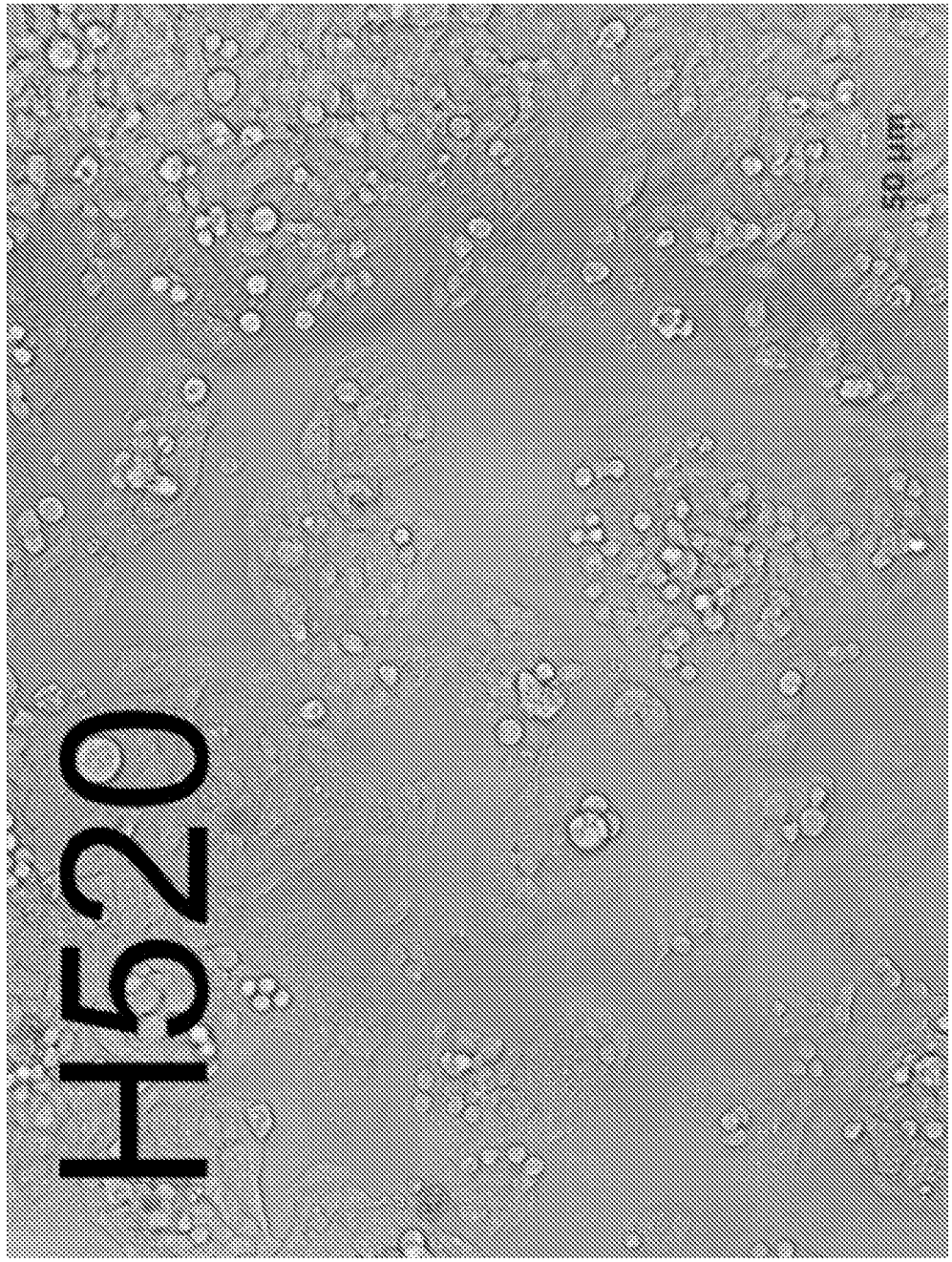
Figure 3D:
Figure 3E:
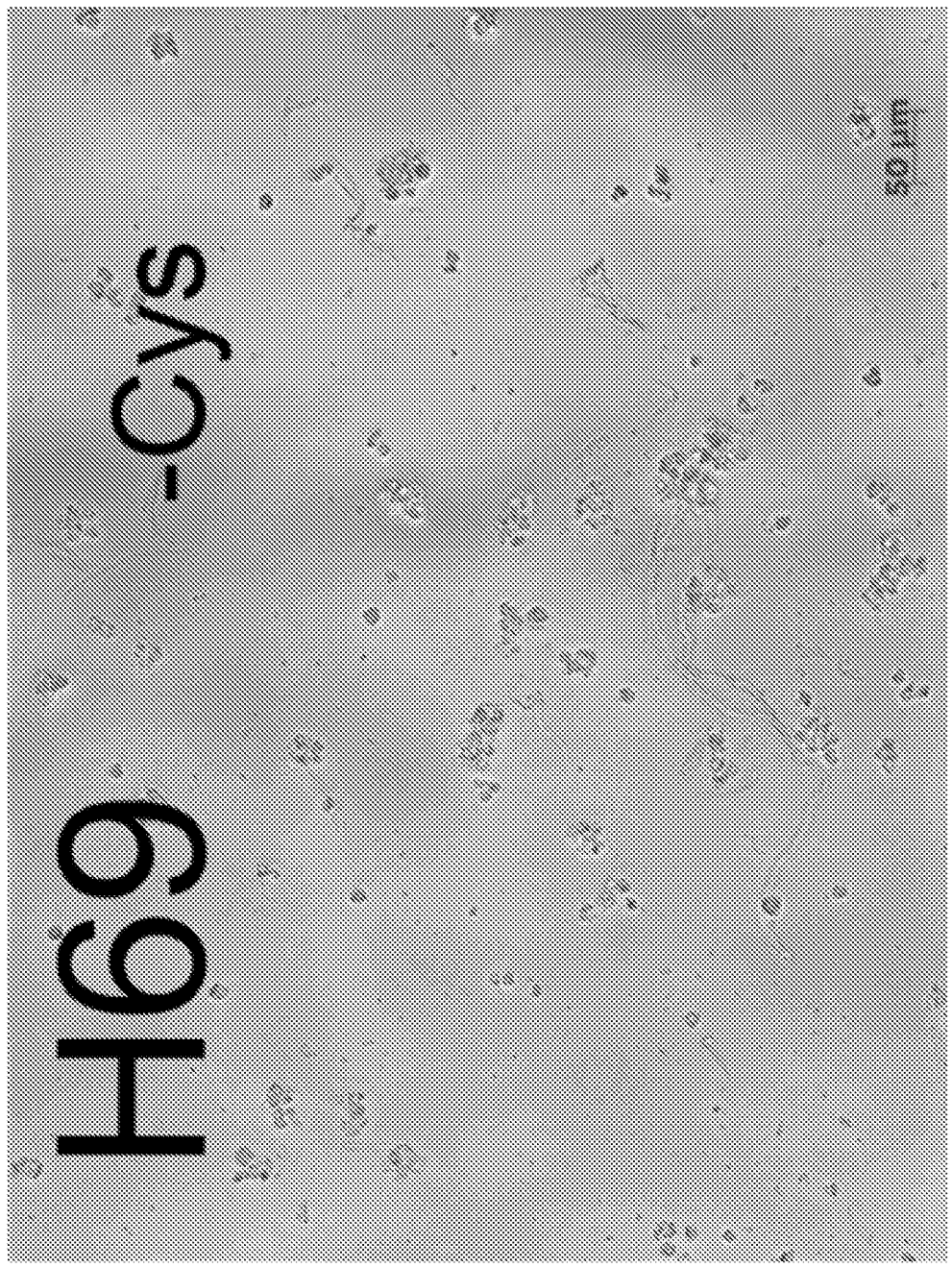
Figure 3F:
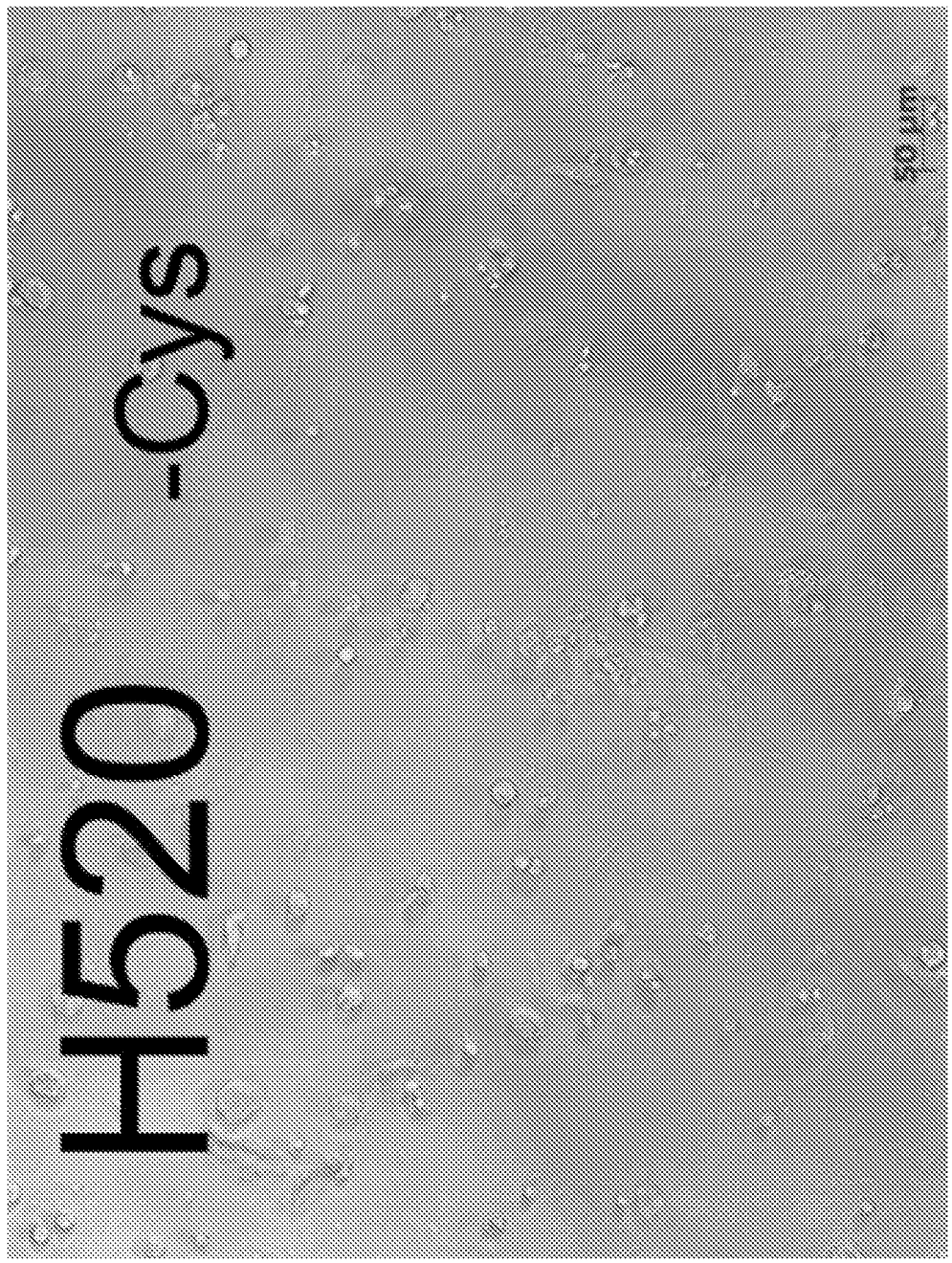
Figure 4A:
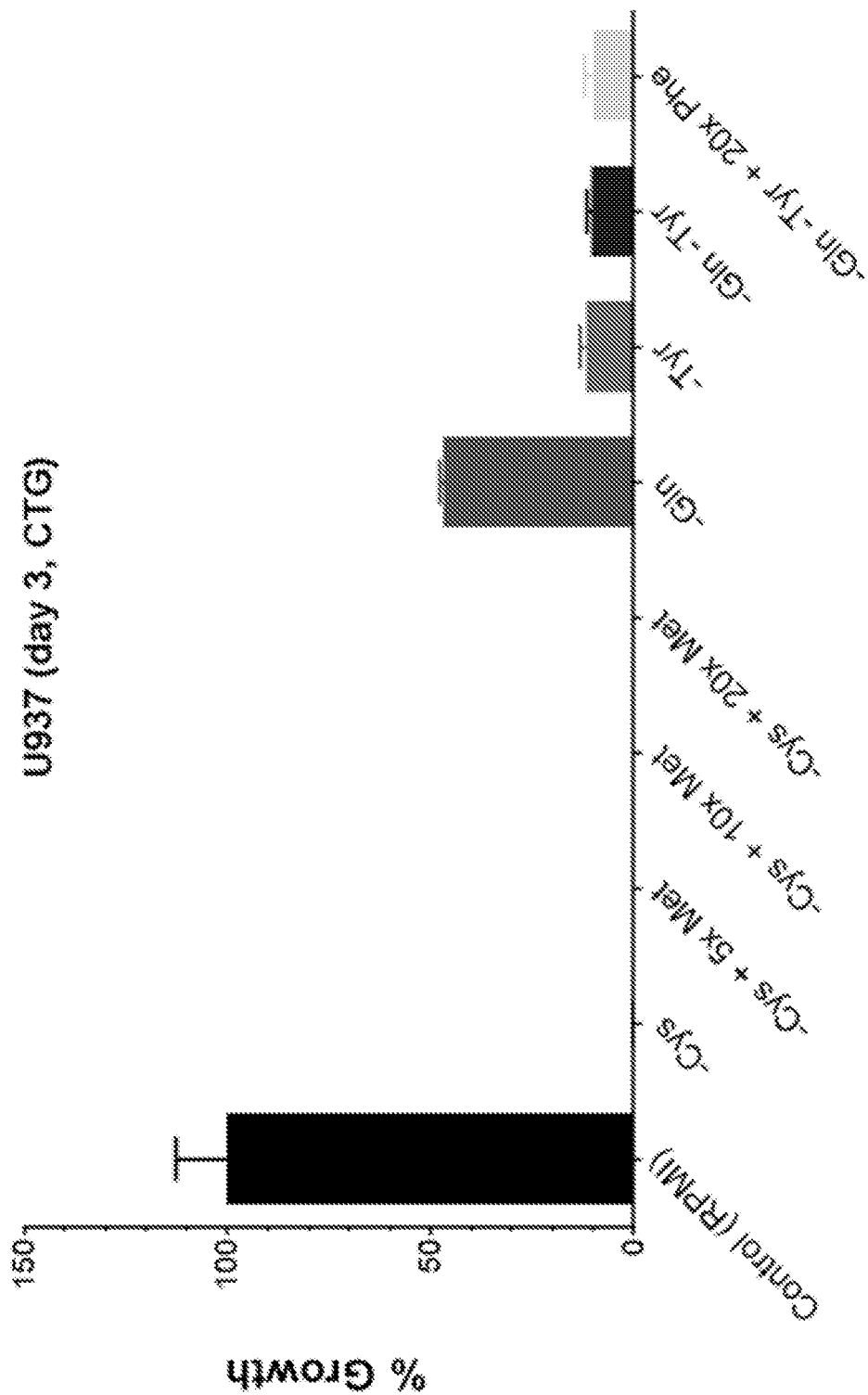
FIGS. 4A-4D show that growth suppression of U937 (FIG. 4A), H661 (FIG. 4B), GA10 (FIG. 4C), and H69 (FIG. 4D) cells by NEAA dropout is not rescued by augmented supplementation of other nutrients. The suppressed growth of cancer cells by dropping out cystine (Cys), glutamine (Gln), tyrosine (Tyr), or double dropout of Gln and Tyr was not improved by adding up to 20 times extra methionine (Met, complementing Cys in normal cells) or phenylalanine (Phe, complementing Tyr in normal cells). Adding 4 times other nonessential amino acids (NEAA), essential amino acids (EAA), or both, also failed to improve suppressed growth by cysteine dropout, results from two biological replicates are shown side by side on each graph in the bottom row. Cell lines are indicated on each graph. The error bars are standard errors of mean of five technical replicates each.
Figure 4B:
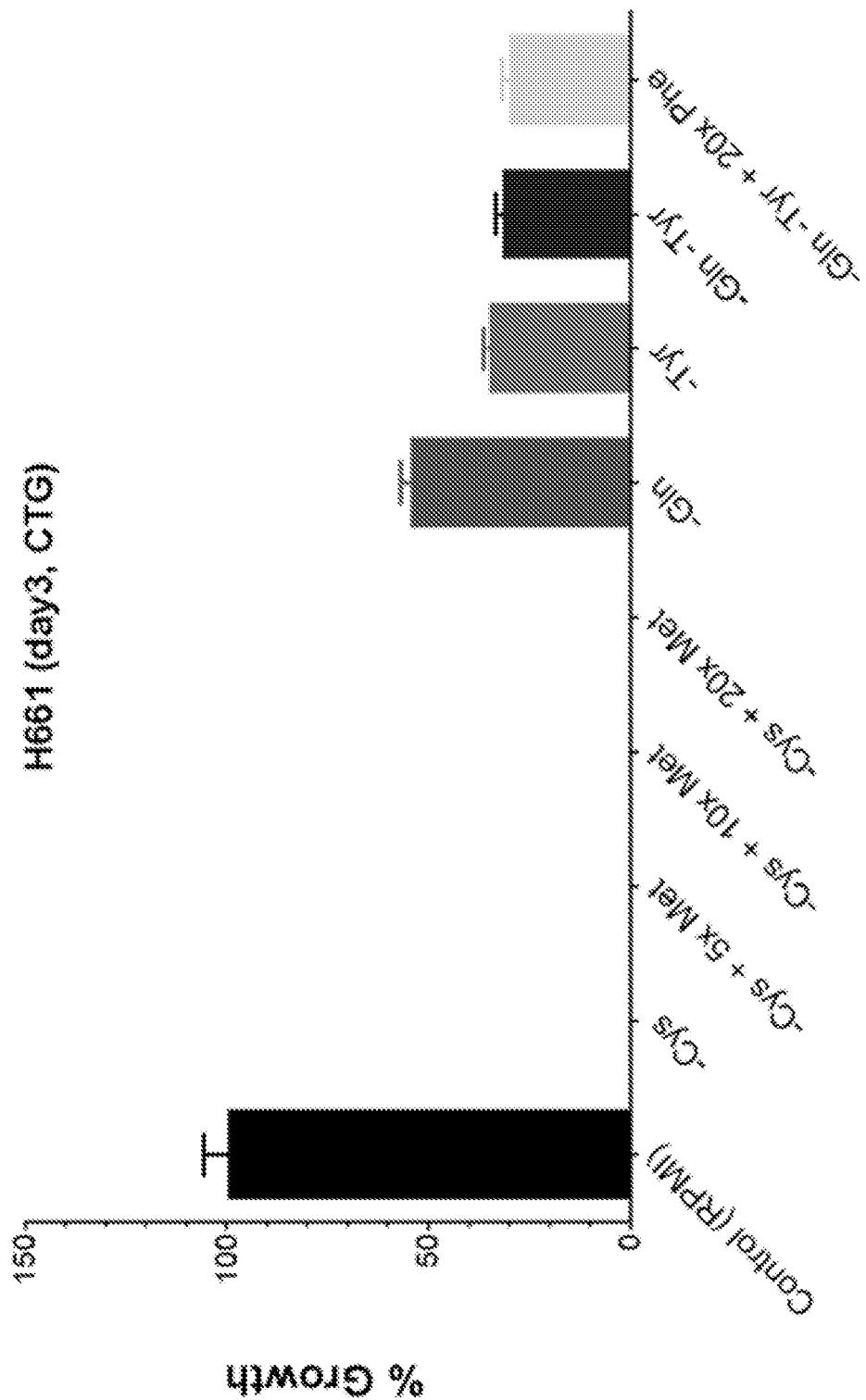
Figure 4C:
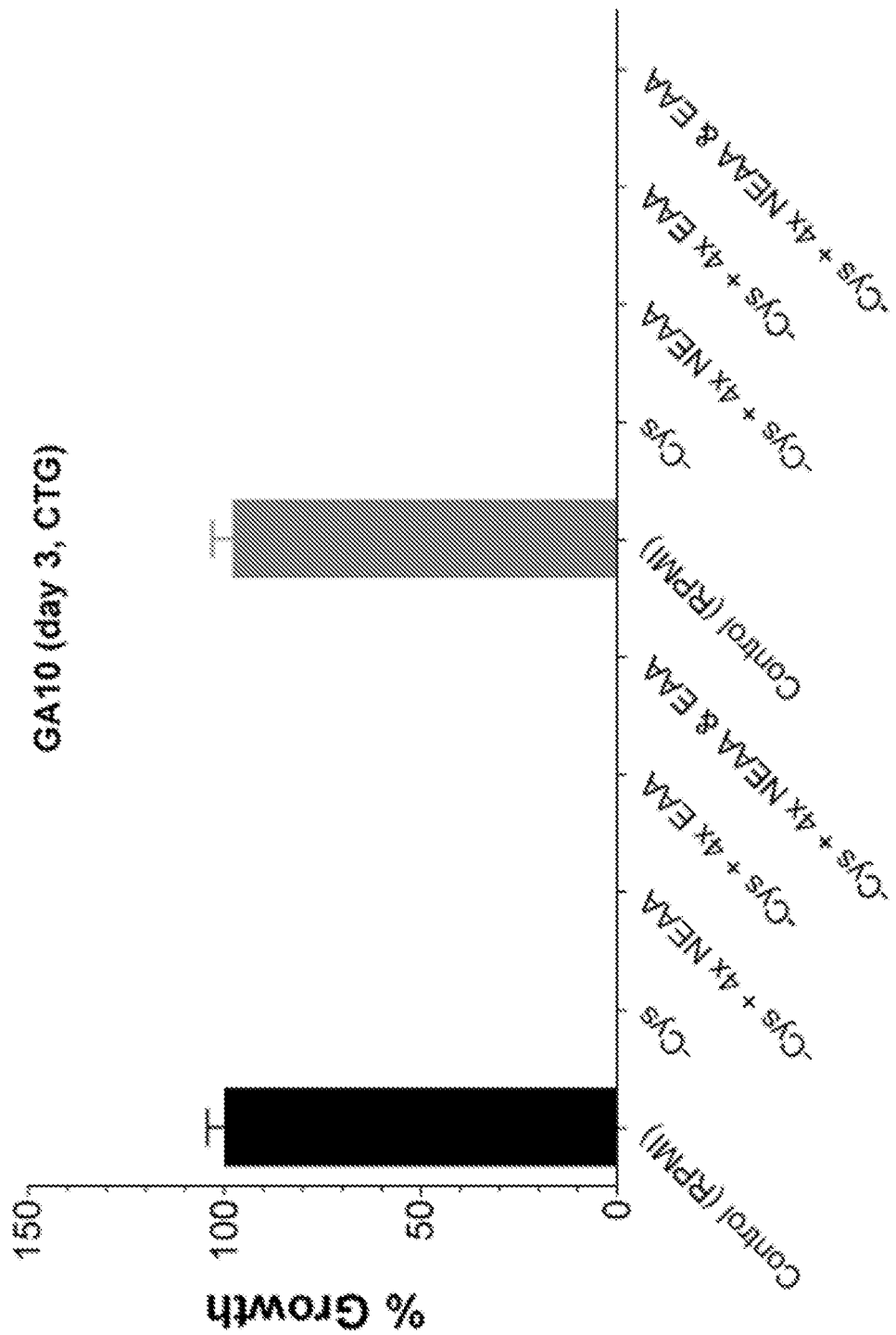
Figure 4D:
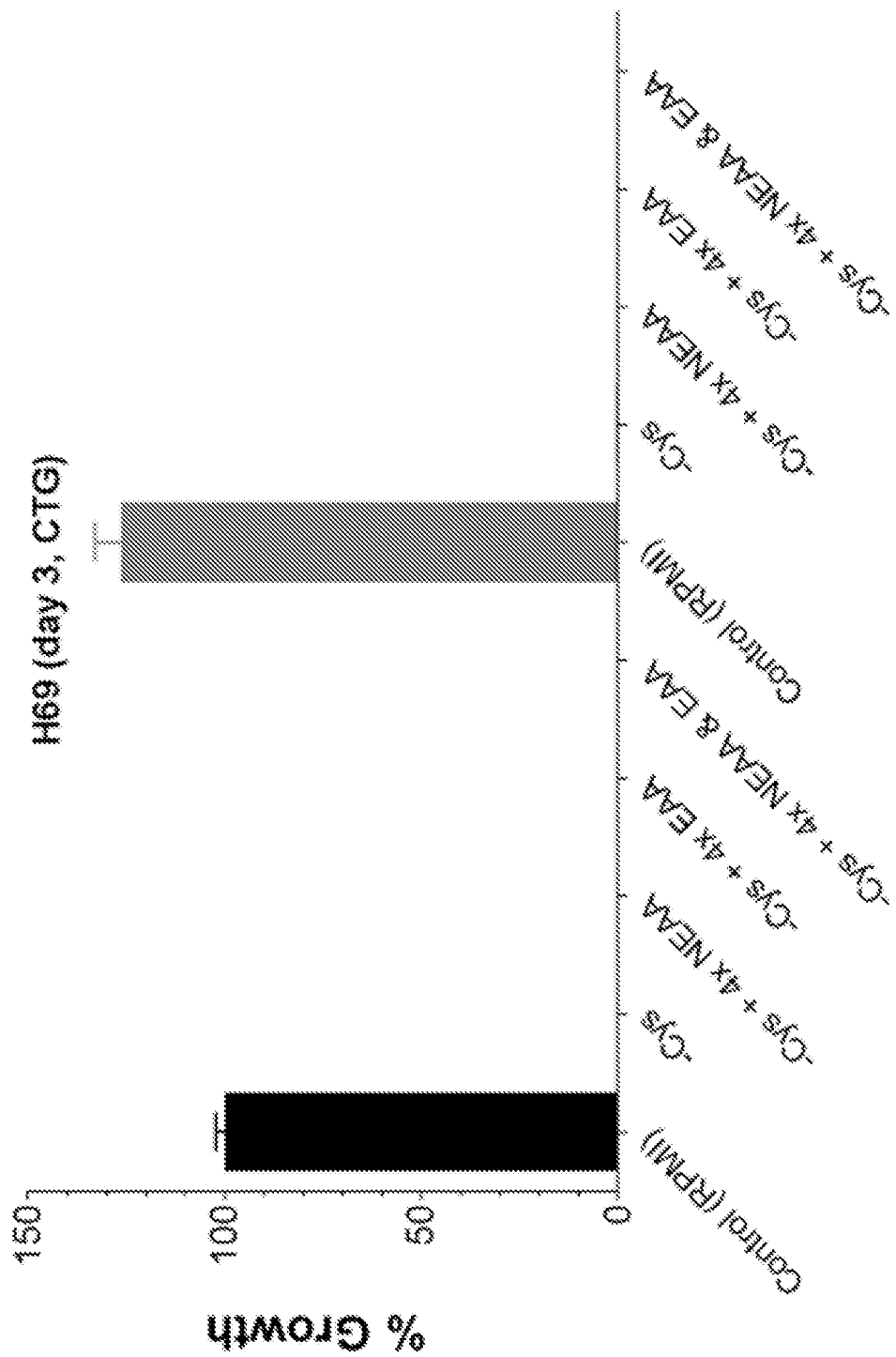

2, Set Up and Analyze Growth Assays
  To test for nutritional weaknesses of cancer cell lines or primary cancer cells, each individual non-essential amino acid was dropped out from the R-comp media (Table 2). Multiple amino acid dropout media was used to test combinatorial effects. Prior to the experiments, cells were first acclimated in R-comp media, and then harvested and washed in EBSS solution. The cell density was adjusted to $1-3 \times 10^5$ cells/ml before adding to equal volumes of 2× dropout media plus 2× R-comp (positive control) in a 96-well plate. The plates were then placed in an incubator set at 37° C. with a 5% $CO_2$ supply. Five technical replicates were used for each medium treatment. For each cell line, at least three biological replicates were performed with 2 time-points (day 1 and day 3). A representative plate layout for testing single dropout media is shown in FIG. 1.

Cell growth was analyzed with two cell viability methods (XTT and CellTiter-Glo-based assays). In the XTT-based assay, cell growth is measured by absorbance at 450 nm after adding the XTT reagent to each culture and incubating under the same culture conditions for 2 hours according to the manufacturer's instructions (ThermoFisher X6493). Absorption at 690 nm was also measured as background and subtracted from absorption at 450 nm. In the CellTiter-Glo-based assay (Promega, G7572), cell growth is measured by luminescence with a dwelling time of 200 milliseconds on a Tecan plate reader.

The relative growth is calculated with the following equation:

$$\text{Growth \%} = (\text{reading}_{dropout} - \text{average}(\text{readings}_{blank})) / (\text{average}(\text{readings}_{R\text{-}comp}) - \text{average}(\text{readings}_{blank})) \times 100\%$$

Results

I) Cancer Cells Exhibit Diverse Patterns of Growth Suppression by Non-Essential Amino Acid Dropouts As shown in FIGS. 2 and 4, the cell growth of different cancers respond to single dropout of non-essential amino acids (NEAA) differentially in both quantitative and qualitative manners. For example, cystine dropout severely and universally suppressed cell growth of all 18 cancer types (except for MDA-MB-453, also see FIG. 5). Dropout of other amino acids, such as arginine (Arg), glutamine (Gln), serine (Ser) and tyrosine (Tyr) had variable suppressive effects on cancer cell growth (FIGS. 2 and 4). Such differences may be attributed to the distinctive metabolisms these cancer cells have adopted along the course of carcinogenesis in different organs and/or in different people. In contrast, normal blood cells (PBMC) were only negligibly affected by any single NEAA dropout in both non-activated and activated states. Similarly, the vitality of human red blood cells were also not affected by cystine restriction or dropout. This observations are consistent with canonical conclusions of the non-essentiality of these amino acids for human health (Rose et al. (1937) Science 86(2231):298-300; Rose (1949) Nutrition Classics. Federation Proceedings 8(2):546-552;

Rose (1976) Nutr. Rev. 34(10):307-309; Young (1994) J. Nutr. 124(8 Suppl):1517S-1523S).

The strongest and most frequent suppression was from cystine (Cys, nutritional equivalent to cysteine) dropout, which suppressed cancer cell growth by greater than 10-fold in all nine cancer cell lines used in this study (FIG. 2). Cancer cells grown in Cys dropout media exhibited cell death as early as day 3 after exposure (FIG. 3), which was marked by inefficient cell clustering of suspension growth (Jurkat and H69) or scarce surface attachment of adhesion growth (H520) (FIG. 3). These morphological characteristics were also observed in other dropout cultures where cell growth was suppressed (not shown), demonstrating NEAA dropouts robustly induced cell death in different types of cancer.

The diversity of cancer-only growth suppression to single NEAA dropout may come from organ origin or personal genetic predispositions (Table 3), which could be clarified by studying more cancer types and more cancer patients of the same type. In both cases, our method provides a robust and precise assay to find the nutritional weaknesses of cancer cells from tumors on a personal basis. The ultimate goal is to use the findings to stop cancer growth with controlled nutritional regimens after integrating our current assay with follow-up dietary intervention. Because no drugs are introduced and only non-essential nutrients are left out, we expect the whole integrative therapy will pose minimal side effects or safety concerns.

2) Cancer Growth Suppression by NEAA Dropout is not Relieved by Augmented Supplementation of Related Nutrients Since metabolism is a highly connected network, many nutritive deficiencies may be compensated without any health problems by augmented supplementation of related metabolites (Rose (1937), supra). For example, cystine may be completely replaced by increased supply of methionine, and tyrosine may be completely compensated by increased phenylalanine (Rose (1937), supra). We then tested if increased supply of certain nutrients could relieve growth suppression of cancer cells by cystine and tyrosine dropouts. The results showed that even with 20 times methionine or phenylalanine, the suppressed growth was not brought back in both leukemia (U937) and lung cancer (H661) (FIG. 4). In fact, methionine was added at up to 50x strength, but still failed to promote the growth of cell lines that were sensitive to cystine dropout (Table 4). The only exception was the human colon cancer line HCT116. Methionine supplementation at 10x was able to substantially restore HCT116 growth in the absence of cystine (Table 4).

Furthermore, the growth suppression by cystine (Cys) dropout was so robust that it was not relieved even by adding 4 times extra of all nine essential amino acids, four times extra of other eight non-essential amino acids, or both, to the media (FIG. 4, bottom row). This strong anti-cancer efficacy from single AA dropout is extremely important for clinical expansion of our invention as a robust nutritional therapy to treat cancer because it has minimal interference from peer nutrients.

We also performed double dropouts of nutrients in the hope of seeing more severe suppression of cancer cell growth. As shown in the top row of FIG. 4, though single dropout of glutamine or tyrosine led to partial growth suppression, omission of them together failed to produce more pronounced growth suppression in leukemia (U937) and lung cancer (H661).

3) Mechanistic Clues to the Robust Growth Suppression by Cystine Dropout

Figure 5:
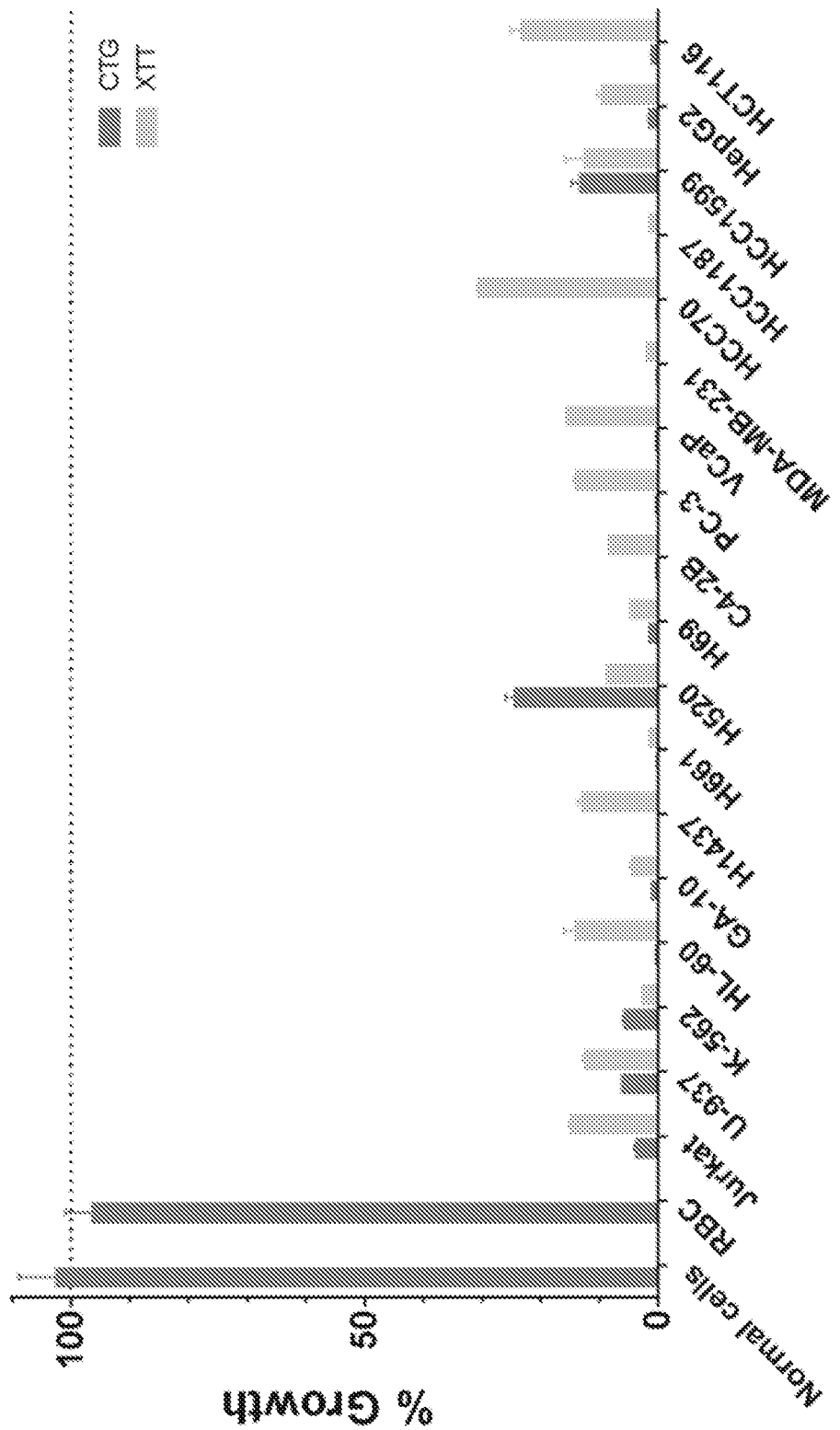
FIG. 5 shows that growth suppression by cystine dropout is dose-dependent. The growth of all cancer cells tested in this study was suppressed by cystine dropout. Normal cells=PBMC. RBC=red blood cells.
Figure 6A:
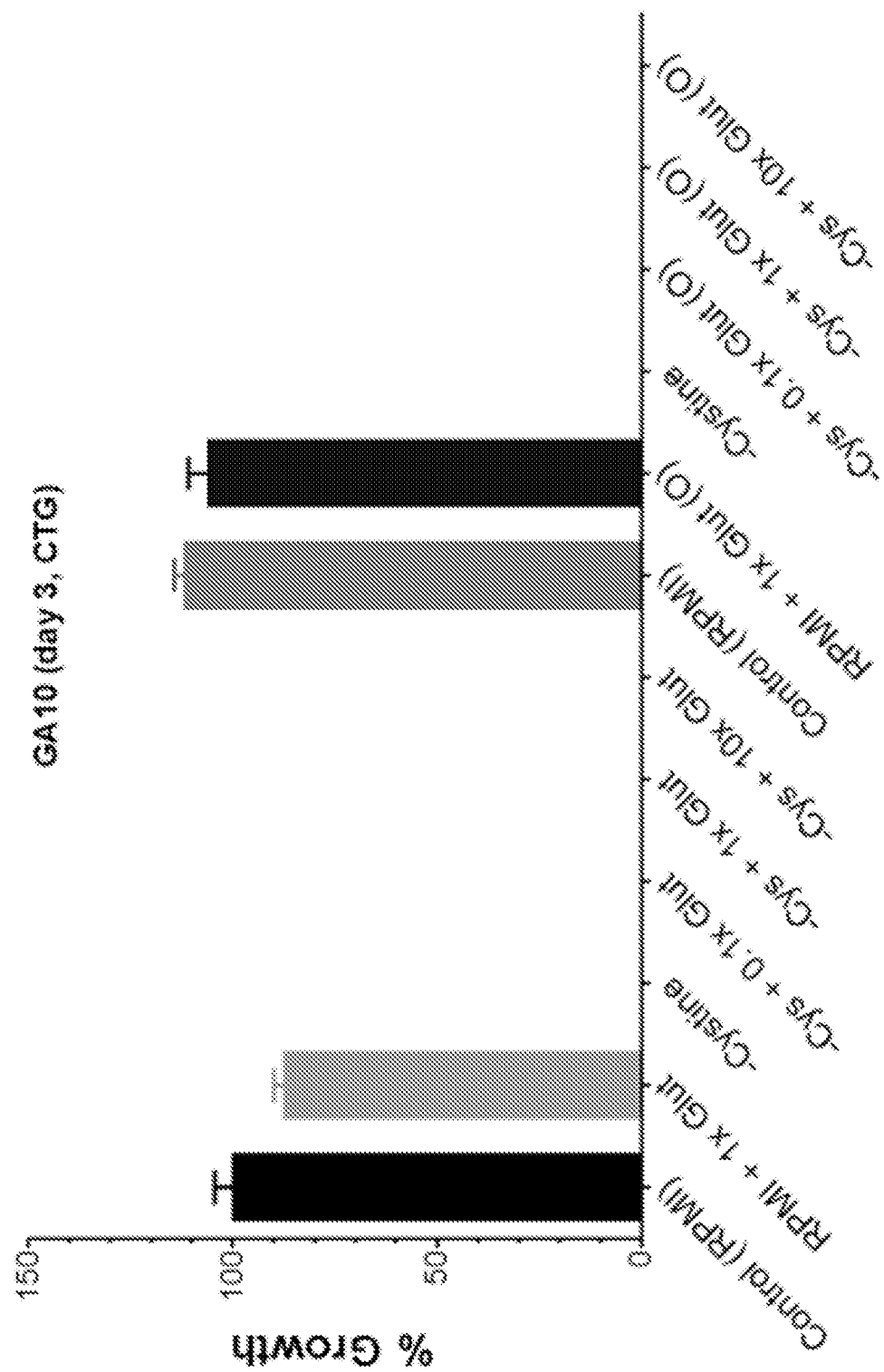
FIGS. 6A-6D show that glutathione partially restores growth, suppressed by cystine dropout, in a redox-dependent manner. Glutathione (Glut) was added to the media at various concentrations in the absence of cysteine. Both the reduced form (Glut) and the oxidized form (Glut (O) were tested. Plots of the relative growth over three days are shown for GA10 (FIG. 6A), H69 (FIG. 6B), Jurkat (FIG. 6C), and H1437 (FIG. 6D) cells. 1× Glut or Glut (O)=1 mg/l. The error bars are standard errors of mean of five technical replicates each.
Figure 6B:
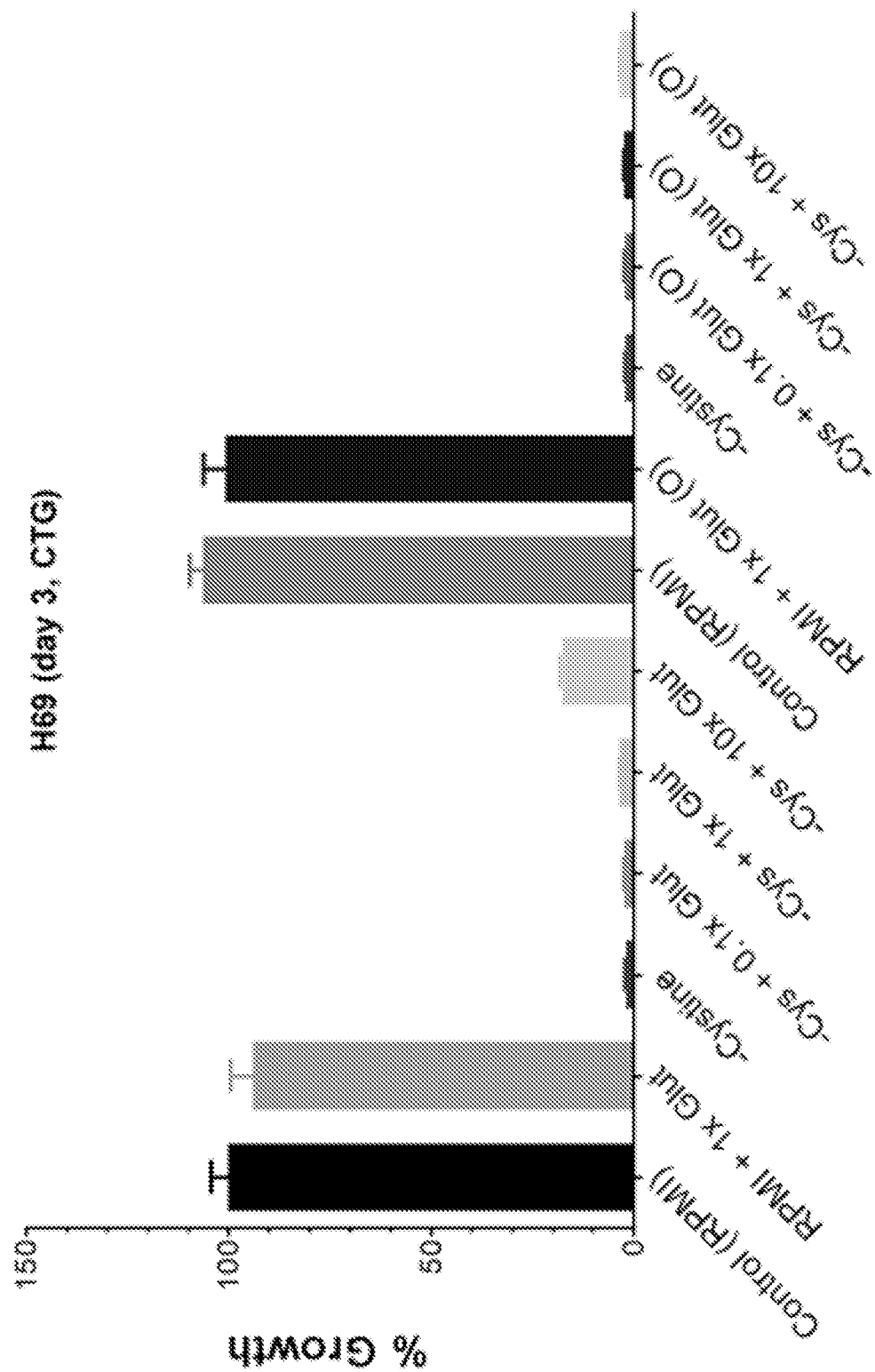
Figure 6C:
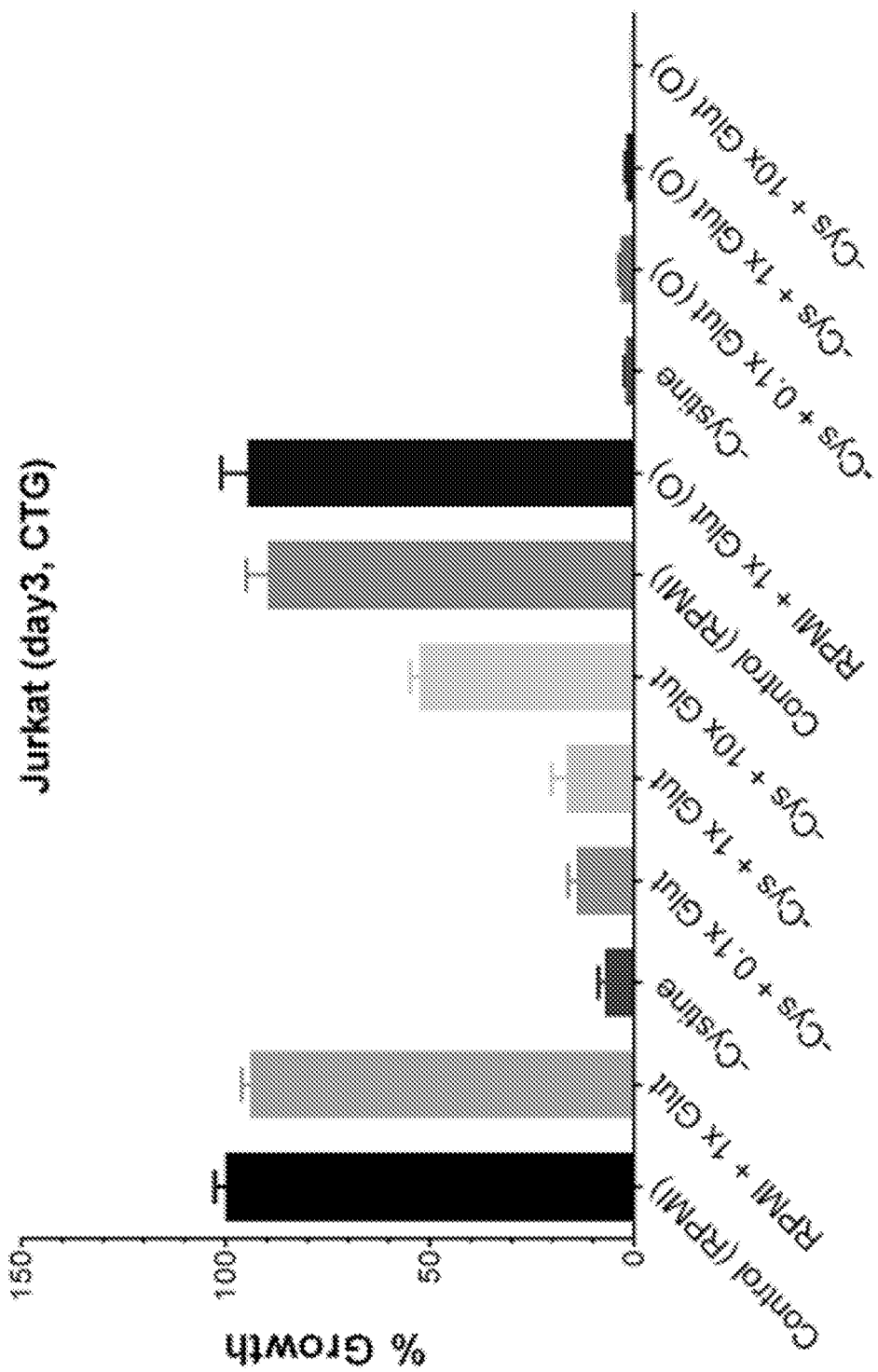
Figure 6D:
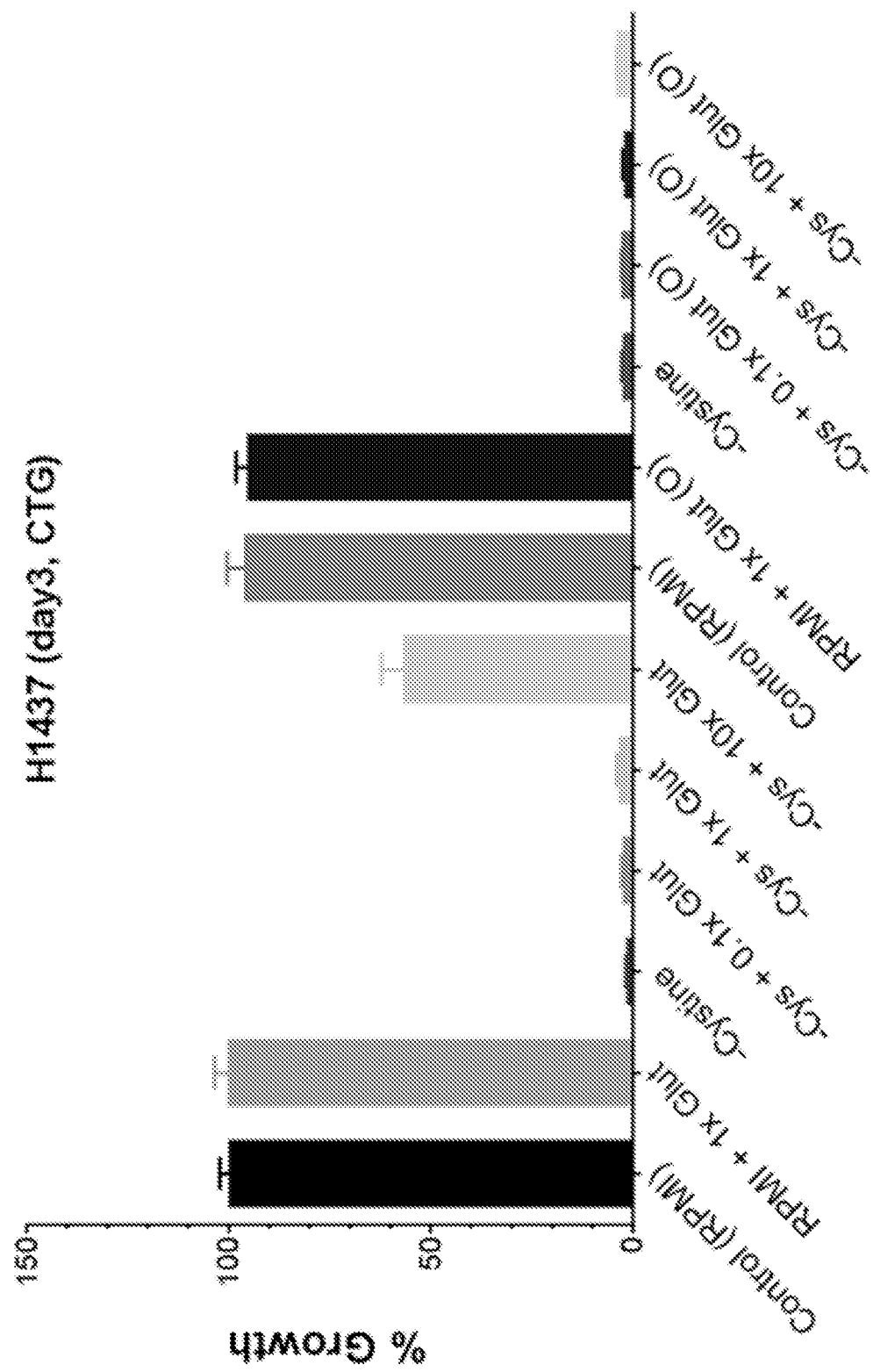

While the severity of growth suppression by individual NEAA dropout varied among cell lines and cell types (Table 3), cystine dropout produced the most prominent effects in all cancer cell lines tested in this study (summarized in FIG. 5). To confirm this effect was only caused by cystine, we added back cystine at several restrictive levels to the media, and compared the quantitative reliance of cancer cells on cystine supply. The results showed that while adding back cystine brought back cell growth to the same level or levels even beyond that of the control, different cancers do exhibit differential quantitative requirements for cystine (Table 4). For instances, at 0.1x level of cystine supplementation, the growth of H520 (lung cancer) was merely restored, whereas the growth of K562 (leukemia) was substantially restored to the levels of the control. These results together validated that the observed growth suppression is caused by cystine deficiency. The dosage sensitivity of cancer cells to cystine may be related to how their metabolism is wired intrinsically.

Cysteine is a precursor to glutathione, a tripeptide metabolite that exists in reduced and oxidized forms to maintain the cellular redox status. It is known that cancer cells, like other fast proliferating cells, have a higher potential to generate reactive oxygen species (ROS) that perturb the cellular redox status and damage cellular components (Cairns et al., supra; Heiden (2011) Nat. Rev. Drug Discov. 10(9):671-684). Thus cancer cells may have an elevated demand for glutathione to compensate for higher flux of ROS, which may explain why cystine dropout severely suppresses cancer cell growth (FIGS. 2 and 6). On the other hand, glutathione may also be hydrolyzed to provide cysteine as nutrients.

Therefore, we tested if reduced glutathione (Glut) or its oxidized form (Glut (O)) could relieve growth suppression by cystine dropout. The results showed that 10x Glut supplementation substantially restored the suppressed growth of some cancer cells, such as Jurkat (leukemia) and H1437 (lung cancer), but not significantly for other cells, such as GA10 (leukemia) and H69 (lung cancer) (Table 4, FIG. 6). Interestingly, the oxidized glutathione lacked the ability to restore suppressed growth in the same cancer cells, suggesting a malfunctioning redox maintenance may play a role in the cancer-only essentiality of cystine. It is thus very likely the observed growth suppression by cystine dropout results from dysregulation of redox status in cancer cells.

A common problem with traditional anticancer drugs is that cancer cells quickly develop resistance. This is not the case for cystine dropout. As shown in FIG. 7, a prolonged 6 month pretreatment with low cystine failed to confer any growth advantage to all tested cancer cell lines under cystine restriction or dropout conditions. These results predict a strong and lasting efficacy in using cystine restriction to treat cancer.

4) Diverse Nutritional Weakness Pattern

Among all 19 cells lines we have tested, the breast cancer cell line MDA-MB-453 was the one that grew almost normally under cystine dropout conditions (FIG. 8). Coincidentally, MDA-MB-453 is non-tumorigenic in immunosuppressed mice (source, ATCC website), suggesting sensitivity to cystine dropout may represent an intrinsic feature of tumor cells. MDA-MB-453 could still be effectively suppressed by increasing the amount of a multivitamin supplement to 50x (Table 5), but its growth was promoted by increasing individual vitamins in the absence of cystine (such as B1 alone, see FIGS. 9 and 10). Similarly, growth of the breast cancer line HCC1599 was substantially restored by adding back vitamin B1 alone (Table 5). For another instance, colon cancer line HCT116 exhibited even more drastic growth suppression when combining cystine dropout and 50× vitamin B2, whereas its growth was largely restored by vitamin B1 supplementation at 50× alone (Table 5). The diversity in nutrient responses again highlights the need and effectiveness of an individualized platform to determine nutritional weakness in developing cancer medicine.

5) Possible Combinatorial Therapy

In cases when dietary restriction of cystine fails to bring down the circulating cystine in time-sensitive cases, cystine-depleting drugs (ifosfamide/mesna) may be used to quickly establish cystine depletion status in patients. Mercaptoethane sulfonate (mesna) has been used in combination with mesna to deplete circulating sulfate-containing methionine, cystine, and glutathione in mice through direct chemical reaction (Lauterburg et al. (1994) Cancer Chemother. Pharmacol. 35(2):132-136).

CONCLUSION

In this study, we have developed a systematic method to determine the nutritional weaknesses of cancer cells. We have discovered diverse patterns of nutritional requirements for non-essential amino acids in nine subtypes of leukemia and lung cancers, but not in normal human cells. The growth sensitivity of cancer cells to non-essential amino acids varies between cancer types and patients, which supports our intention to perform this assay on a personal basis, rather than use it merely as a research tool for discovery of new general anti-cancer targets (despite its application in this regard as well).

With minor modification of the recipe to accommodate specific nutritional requirements of individual tumor cells, our method may be expanded to clinical biopsies to determine the nutritional weaknesses of other cancers on a personal basis, for use in formulating a nutritional regimen to stop cancer growth. In that respect, our method may be implemented in a clinical service.

Therapeutic implementation of our method may have the following advantages:

1) Great safety, minimal side effects. No artificial drugs are included. Proven and re-proven nutritional non-essentiality of amino acids in humans.

2) Robust efficacy. Substantial suppression of cancer growth is expected with minimal interference from other nutrients and minimal tolerance/resistance.

3) Expansion-friendly. Other groups of nutrients, such as choline and vitamins, may be conveniently incorporated into existing tests as upgrades for better chances of finding a nutritional weakness of cancer cells.

4) Personal basis. The business mode comes in the form of clinical services that may combine screening and personalized cancer therapy.

TABLE 1

List of cancer cell lines that have been tested.

| Cell Line | Origin | Gender | |
|---|---|---|---|
| Blood cancer | | | |
| Jurkat | T lymphocyte | acute T cell leukemia (ALL) | male |
| U-937 | monocyte | histiocytic lymphoma (non-Hodgkin lymphomas, CLL) | male |

TABLE 1-continued

List of cancer cell lines that have been tested.

| Cell Line | Origin | Gender | |
|---|---|---|---|
| K-562 | bone marrow | Chronic myeloid leukemia (CML) | female |
| HL-60 | promyeloblast | acute promyelocytic leukemia (AML) | female |
| GA-10 | B lymphocyte | Burkitt's lymphoma | male |
| Lung cancer | | | |
| NCI-H1437 | NSCLC | stage 1, adenocarcinoma; non-small cell lung cancer | male |
| NCI-H661 | NSCLC | carcinoma; large cell lung cancer | male |
| NCI-H520 | NSCLC | squamous cell carcinoma | male |
| NCI-H69 | SCLC | carcinoma; small cell lung cancer | male |
| Liver cancer | | | |
| HepG2 | HCC | hepatocellular carcinoma | male |
| Breast cancer | | | |
| MDA-MB-453 | LAR | metastatic carcinoma | female |
| MDA-MB-231 | MSL | adenocarcinoma | female |
| HCC70 | BL2 | primary ductal carcinoma | female |
| HCC1599 | BL1 | primary ductal carcinoma | female |
| HCC1187 | IM | primary ductal carcinoma | female |
| Prostate cancer | | | |
| PC-3 | | adenocarcinoma | male |
| C4-2B | LN-CaP derived | bone metastatic from prostate carcinoma | male |
| VCaP | | hormone refractory prostate cancer | male |
| Colon cancer | | | |
| HCT116 | | colorectal carcinoma | male |

ALL, acute lymphoblastic leukemia; CLL, chronic lymphoblastic leukemia; CML, chronic myeloid leukemia; AML, acute myeloid leukemia; NSCLC, non-small cell lung cancer; SCLC, small cell lung cancer; HCC, human hepatocellular carcinoma; LAR, luminar androgen receptor, BL1: basal-like 1; MSL, mesenchymal stem-like; BL2, basal-like 2; IM, immunomodulatory.

TABLE 2

Recipe of the reconstituted RPMI complete medium (R-comp).

| Components | Vendor | Cat. No. | Final |
|---|---|---|---|
| Earle's Balanced Salt Solution (EBSS) | Invitrogen | 14155-063 | 1x |
| Calcium Chloride (CaCl$_2$) | Sigma | C5670 | 1.8 mM |
| Magnesium Sulfate (MgSO$_4$) | EMD | MX0045-1 | 0.814 mM |
| Fetal Bovine Serum, Dialyzed | Invitrogen | 26400-044 | 10% |
| MEM vitamin Solution | Invitrogen | 11120-052 | 1x |
| Antibiotics (penicillin and streptomycin) | Invitrogen | 15140-122 | 100 u/ml |
| Essential Amino acids (EAAs) | | | |
| Histidine | Sigma | H5659-25G | 0.10 mM |
| Isoleucine | Sigma | I7403-25G | 0.38 mM |
| Leucine | Sigma | L8912-25G | 0.38 mM |
| Lysine | Sigma | L8662-25G | 0.27 mM |
| Methionine | Sigma | M5308-25G | 0.10 mM |
| Phenylalanine | Sigma | P5482-25G | 0.09 mM |
| Threonine | Sigma | 18441-25G | 0.17 mM |
| Tryptophan | Sigma | 8941-25G | 0.02 mM |
| Valine | Sigma | V0513-25G | 0.17 mM |
| Non-essential Amino Acids (NEAAs, may be dropped out) | | | |
| Alanine | Sigma | A7469-25G | 0.20 mM |
| Arginine | Sigma | A6969-25G | 1.15 mM |
| Asparagine | Sigma | A4159-25G | 0.38 mM |
| Aspartate | Sigma | A7219-100G | 0.15 mM |
| Cysteine (Cystine*) | Sigma | C7602-25G | 0.21 mM |
| Glutamate | Sigma | G8415-100G | 0.14 mM |
| Glutamine | Sigma | G8540-25G | 2.05 mM |
| Glycine | Sigma | G8790-100G | 0.13 mM |
| Proline | Sigma | P5607-25G | 0.17 mM |

TABLE 2-continued

Recipe of the reconstituted RPMI complete medium (R-comp).

| Components | Vendor | Cat. No. | Final |
|---|---|---|---|
| Serine | Sigma | S4311-25G | 0.29 mM |
| Tyrosine | Sigma | T8566-25G | 0.11 mM |

In case of a non-essential amino acid is dropped out, equal volume of EBSS is added.
*Cystine is equivalent to cysteine in nutrition.

TABLE 3

Summary of relative growth of cancer cells in NEAA dropout media.

| Cell Line | —Ala | —Arg | —Asp | —Asn | —Cys | —Glu | —Gln | —Gly | —Pro | —Ser | —Tyr |
|---|---|---|---|---|---|---|---|---|---|---|---|
| GA10 | 90.6 | 29.1 | 56.7 | 99.7 | 6.0 | 31.0 | 38.1 | 87.6 | 105.6 | 46.6 | 22.1 |
| HL60 | 98.0 | 26.2 | 94.1 | 94.2 | 0.1 | 104.3 | 9.4 | 112.8 | 54.8 | 56.2 | 16.3 |
| Jurkat | 96.6 | 58.6 | 104.6 | 120.5 | 1.5 | 128.3 | 33.2 | 108.3 | 113.4 | 101.7 | 44.7 |
| K562 | 103.6 | 48.8 | 113.6 | 112.9 | 0.0 | 108.1 | 23.7 | 101.1 | 104.4 | 77.9 | 41.7 |
| U937 | 97.6 | 32.4 | 96.0 | 95.3 | 0.0 | 102.6 | 14.7 | 92.6 | 96.3 | 98.9 | 34.3 |
| H1437 | 100.9 | 48.9 | 86.4 | 88.5 | 0.2 | 25.8 | 32.5 | 96.7 | 96.5 | 60.5 | 51.9 |
| H520 | 101.6 | 33.2 | 110.1 | 95.8 | 7.9 | 103.8 | 22.3 | 95.6 | 60.7 | 80.6 | 34.6 |
| H661 | 98.9 | 24.8 | 106.6 | 101.9 | 5.0 | 107.5 | 21.0 | 107.7 | 113.1 | 53.9 | 20.4 |
| H69 | 89.8 | 29.5 | 89.1 | 72.1 | 2.4 | 93.6 | 24.3 | 95.2 | 99.0 | 37.9 | 18.6 |
| HepG2 | 73.6 | 35.0 | 97.7 | 104.3 | 9.7 | 109.8 | 64.8 | 106.2 | 86.7 | 76.0 | 48.4 |
| MDA-MB-453 | 91.4 | 98.0 | 99.5 | 106.8 | 76.2 | 121.5 | 118.4 | 119.6 | 108.7 | 112.3 | 92.2 |
| MDA-MB-231 | 94.9 | 54.8 | 108.1 | 106.6 | 0.1 | 114.8 | 41.4 | 94.3 | 100.1 | 45.2 | 43.5 |
| HCC70 | 92.7 | 63.4 | 101.6 | 112.3 | 0.3 | 107.2 | 74.7 | 98.0 | 113.6 | 132.1 | 53.0 |
| HCC1599 | 106.6 | 94.5 | 92.6 | 98.4 | 19.1 | 99.8 | 91.7 | 83.9 | 88.8 | 91.9 | 85.5 |
| HCC1187 | 101.3 | 82.0 | 107.4 | 116.7 | 0.1 | 115.3 | 82.9 | 110.9 | 101.5 | 105.3 | 33.5 |
| PC-3 | 125.7 | 60.1 | 133.5 | 123.6 | 0.3 | 128.5 | 49.8 | 104.3 | 123.3 | 121.1 | 55.6 |
| C4-28 | 90.3 | 78.7 | 94.7 | 108.2 | 8.6 | 105.1 | 107.6 | 98.9 | 106.5 | 94.3 | 61.1 |
| VCaP | 102.2 | 115.7 | 116.4 | 134.0 | 0.5 | 136.0 | 54.0 | 131.1 | 129.5 | 141.1 | 77.9 |
| HCT116 | 103.9 | 154.5 | 107.9 | 112.1 | 2.2 | 108.2 | 70.5 | 152.7 | 103.3 | 164.3 | 57.2 |
| PBMC | 95.4 | 103.5 | 113.6 | 112.6 | 102.3 | 121.9 | 98.7 | 116.0 | 116.9 | 88.3 | 109.4 |
| PBMC-ac | 96.8 | 73.7 | 106.2 | 89.1 | 71.2 | 111.0 | 80.4 | 92.8 | 105.8 | 72.7 | 79.4 |

Values are average relative growth (in %) from more than 3 biological replicates in eleven dropout media over three days. Growth in complete media was set to 100%. Gray shades indicate the extent of growth suppression by number scales. Left, CellTiter-Glo assay. Right, XTT assay. PBMC, human peripheral blood mononuclear cells (primary blood cells capable of proliferation in vitro, as normal cell control, n = 4). PBMC-ac, activated PBMC with 5 µg/ml

TABLE 4

Growth suppression by cystine dropout is dose-dependent

| | +Cys (5x Met) | | | | | —Cys | | | | | |
|---|---|---|---|---|---|---|---|---|---|---|---|
| | | | | | | +Met | | | +Glut | | |
| Cell Line | 0.5x | 0.1x | 0.05x | 0.02x | 0.01x | 10x | 50x | 2.5x | 10x | 50x | 100x |
| GA10 | 12.0 | 18.4 | 19.5 | 20.5 | 18.4 | 17.1 | 15.5 | 20.0 | 17.2 | 18.0 | 17.1 |
| HL60 | 107.6 | 12.1 | 4.3 | 1.6 | 0.8 | 0.4 | 0.4 | 20.9 | 124.4 | 101.0 | 104.6 |
| Jurkat | 93.3 | 0.4 | 0.4 | 0.4 | 0.4 | 0.4 | 0.6 | 0.4 | 32.7 | 74.0 | 77.7 |
| K562 | 101.5 | 36.5 | 9.5 | 2.2 | 1.9 | 1.6 | 1.1 | 16.2 | 78.8 | 84.4 | 98.9 |
| U937 | 104.4 | 0.2 | 0.1 | 0.0 | 0.0 | 0.0 | 0.0 | 0.1 | 48.7 | 107.1 | 104.7 |
| H1437 | 93.8 | 3.2 | 0.7 | 0.4 | 0.6 | 0.5 | 0.7 | 0.8 | 29.6 | 50.1 | 64.1 |
| H520 | 110.4 | 41.8 | 9.4 | 4.7 | 5.2 | 7.3 | 16.7 | 21.3 | 71.3 | 97.8 | 105.7 |
| H661 | 103.2 | 0.1 | 0.1 | 0.1 | 0.1 | 0.1 | 0.1 | 0.2 | 13.0 | 75.4 | 41.1 |
| H69 | 51.8 | 2.1 | 1.2 | 1.3 | 1.2 | 1.2 | 1.2 | 1.4 | 2.1 | 3.6 | 2.8 |
| HepG2 | 92.0 | 3.3 | 3.3 | 3.6 | 4.2 | 4.6 | 3.5 | 4.1 | 105.9 | 100.0 | 94.5 |
| MDA-MB-453 | 102.0 | 91.5 | 91.6 | 79.9 | 82.4 | 73.8 | 73.3 | 70.3 | 94.6 | 91.6 | 97.4 |
| MDA-M8-231 | 80.4 | 0.5 | 0.4 | 0.3 | 0.3 | 0.4 | 0.4 | 0.4 | 3.2 | 27.8 | 29.3 |
| HCC70 | 88.5 | 24.5 | 8.8 | 6.0 | 5.4 | 5.1 | 4.2 | 6.5 | 38.6 | 72.6 | 82.8 |
| HCC1599 | 85.2 | 40.0 | 27.1 | 16.5 | 17.1 | 19.9 | 9.6 | 29.5 | 49.2 | 73.5 | 69.0 |
| PC-3 | 76.6 | 12.0 | 3.8 | 2.8 | 1.5 | 1.9 | 1.9 | 2.2 | 31.9 | 64.3 | 66.1 |
| C4-28 | 96.5 | 1.1 | 0.3 | 0.3 | 0.2 | 0.3 | 0.2 | 0.5 | 74.0 | 140.4 | 134.4 |
| VCaP | 87.7 | 1.4 | 0.7 | 0.6 | 0.6 | 0.7 | 0.6 | 2.2 | 80.8 | 96.5 | 90.3 |
| HCT116 | 93.6 | 134.8 | 101.8 | 80.2 | 77.7 | 72.8 | 40.8 | 122.0 | 96.9 | 93.8 | 92.6 |

A. The growth of all cancer cells tested in this study are suppressed by cystine dropout.
Normal cells = PBMC.
RBC = red blood cells.
B. Values are average relative growth (in %) from 2-3 biological replicates in eleven dropout media over three days. Growth in complete media was set as 100%. Blue shades indicate the extent of growth suppression by number scales. Media with 5x Met contain the same amount of sulfur as complete media. Results shown above were from CellTiter-Glo assays.

TABLE 5

Summary of relative growth of cancer cells in media with cystine (Cys) dropout and vitamin supplementation.

| | —Cys | | | | | | | | | | |
|---|---|---|---|---|---|---|---|---|---|---|---|
| | Vitamin Mix | | | +Vitamin B (50x) | | | | | | | |
| Cell Line | — | 5x | 25x | 50x | B1 | B2 | B3 | B5 | B6 | B7 | B9/B12 |
| GA10 | 2.8 | 4.2 | 11.7 | 19.0 | 8.6 | 8.1 | 3.1 | 4.3 | 3.6 | 3.8 | 6.0 |
| HL60 | 0.0 | 0.2 | 0.2 | 0.1 | 1.4 | 0.0 | 0.2 | 0.1 | 0.0 | 0.0 | 0.0 |
| Jurkat | 0.3 | 0.3 | 0.3 | 0.3 | 0.4 | 0.3 | 0.3 | 0.3 | 0.3 | 0.3 | 0.3 |
| U937 | 0.0 | 0.1 | 0.0 | 0.0 | 0.0 | 0.0 | 0.0 | 0.0 | 0.0 | 0.0 | 0.0 |
| H1437 | 0.4 | 0.5 | 1.0 | 1.6 | 0.6 | 0.8 | 0.5 | 0.5 | 0.4 | 0.4 | 0 5 |
| H520 | 0.2 | 0.3 | 0.3 | 0.4 | 0.5 | 0.3 | 0.3 | 0.3 | 0.2 | 0.2 | 02 |
| H661 | 0.2 | 0.2 | 0.7 | 0.7 | 1.5 | 0.2 | 0.2 | 0.2 | 0.9 | 0.2 | 0.8 |
| H69 | 5.0 | 4.3 | 4.7 | 4.1 | 5.8 | 5.0 | 5.3 | 5.5 | 5.2 | 5.7 | 5.5 |
| HepG2 | 0.7 | 3.1 | 8.8 | 9.0 | 8.2 | 1.5 | 1.8 | 1.4 | 0.8 | 1.1 | 1.4 |
| MDA-MB-453 | 92.5 | 83.1 | 38.7 | 18.0 | 118.5 | 45.1 | 96.0 | 104.4 | 70.7 | 91.6 | 75.6 |
| MDA-MB-231 | 0.2 | 0.2 | 0.1 | 0.2 | 0.3 | 0.2 | 0.2 | 0.2 | 0.2 | 0.2 | 0.2 |
| HCC70 | 0.5 | 1.5 | 2.6 | 0.2 | 4.9 | 1.1 | 1.5 | 0.9 | 0.3 | 1.2 | 1.2 |
| HCC1599 | 3.1 | 11.8 | 3.3 | 3.6 | 49.2 | 4.1 | 13.2 | 4.9 | 2.9 | 6.7 | 9.1 |
| HCC1187 | 8.2 | 1.8 | 4.6 | 1.2 | 6.2 | 1.0 | 3.4 | 0.0 | 2.2 | 5.8 | 4.4 |
| PC-3 | 0.4 | 0.7 | 0.5 | 0.5 | 2.6 | 0.3 | 0.0 | 0.8 | 0.2 | 1.2 | 1.0 |
| C4-28 | 0.2 | 0.2 | 0.1 | 0.1 | 0.5 | 0.2 | 0.1 | 0.2 | 0.2 | 0.1 | 0.2 |
| VCaP | 0.1 | 0.1 | 0.1 | 0.0 | 3.3 | 0.1 | 0.1 | 0.1 | 0.1 | 0.2 | 0.2 |
| HCT116 | 22.7 | 24.7 | 0.4 | 0.7 | 82.3 | 0.6 | 52.8 | 56.4 | 47.5 | 27.5 | 24.5 |

Values are average relative growth (in %) from 2-3 biological replicates in eleven dropout media over three days. Growth in complete media was set as 100%. Gray shades indicate the extent of growth suppression by number scales. All Cys dropout Media contain 5x Met and thus the same amount of sulfur as complete media. Vitamin mix contains biotin (B7), choline, calcium pantothenate (B5), folic acid (89), niacinamide (83), para-aminobenzoic acid, pyridoxine (66), riboflavin (82), thiamine (81), cobalamin (B12), i-Inositol at indicated strength as compared to complete media. Individual vitamin B was supplemented at 50x strength. B9/B12 were combined in the last treatment. Results shown above were from Cell-Titer-Glo assays.

While the preferred embodiments of the invention have been illustrated and described, it will be appreciated that various changes can be made therein without departing from the spirit and scope of the invention.

What is claimed is:

1. A method for treating a subject for cancer, the method comprising putting the subject having the cancer on a low-cysteine diet that reduces or eliminates the subject's daily intake of food containing cysteine or cystine, wherein the cancer is responsive to the low-cysteine diet, and wherein said low-cysteine diet comprises protein-free food and an amino add-containing supplement comprising all of the essential amino adds including histidine, isoleucine, leucine, lysine, methionine, phenylalanine, threonine, tryptophan, and valine.

2. The method of claim 1, wherein the low-cysteine diet reduces the subject's daily intake of foods containing cysteine or cystine by at least 80%.

3. The method of claim 1, wherein the subject stays on the diet for at least 1-4 months.

4. The method of claim 1, wherein the low-cysteine diet reduces or eliminates the subject's daily intake of cysteine-containing proteins.

5. The method of claim 1, wherein the low-cysteine diet provides other nutrients at levels in accordance with United States Recommended Daily Allowances (USRDA) guidelines.

6. The method of claim 1, wherein the cancer is lung cancer, liver cancer, breast cancer, prostate cancer, colon cancer, lymphoma, or leukemia.

7. The method of claim 1 wherein said putting the subject on a low-cysteine diet comprises providing the subject with dietary instructions for said low cysteine diet or providing the subject with cysteine-free meals.

8. The method of claim 1, further comprising prescribing an amino acid-containing supplement comprising all of the essential amino acids including histidine, isoleucine, leucine, lysine, methionine, phenylalanine, threonine, tryptophan, and valine.

9. The method of claim 1, further comprising reducing or eliminating the subject's daily intake of one or more amino acids selected from the group consisting of arginine, glutamine, serine, and tyrosine.

10. The method of claim 1, further comprising reducing the subject's daily intake of vitamin B1.

11. The method of claim 1, further comprising treating the subject with an effective amount of a multivitamin at a dosage sufficient to further reduce growth of the cancer.

12. The method of claim 11, wherein the dosage of the multivitamin is 5 to 50 times the amount recommended by the USRDA guidelines.

13. The method of claim 1, further comprising treating the subject with an effective amount of vitamin B2 at a dosage sufficient to further reduce growth of the cancer.

14. The method of claim 1, wherein the subject is a mammal.

15. The method of claim 14, wherein the subject is human.

16. The method of claim 1, wherein the low-cysteine diet is continued until at least a partial tumor response is effected.

17. The method of claim 16, wherein the low-cysteine diet is continued until a complete tumor response is effected.

18. The method of claim 1, further comprising monitoring levels of cysteine or cystine in blood of the subject in order to determine how to adjust the diet of the subject to reduce the levels of the cysteine or cystine sufficiently to suppress growth of the cancer.

19. The method of claim 1, further comprising administering to the subject at least one therapeutic agent that further reduces cysteine or cystine levels in the bloodstream or intracellularly in cancer cells of the subject.

20. The method of claim 19, wherein said at least one therapeutic agent is selected from the group consisting of a cytsteine/cystine-depleting drug, a cysteine degradation enzyme, a gamma-glutamyl transpeptidase inhibitor, a cysteine/cystine transporter inhibitor, and an inhibitor of cysteine biosynthesis.

21. The method of claim 20, wherein said at least one therapeutic agent is mercaptoethane sulfonate (mesna) or ifosfamide, or a combination thereof.

22. The method of claim 1, wherein the responsiveness of the cancer is determined by a suppressed growth of cancerous cells from the subject in cysteine dropout media having all essential amino acids for growth of a normal cell, but deficient in cysteine, as compared to the cell growth in a corresponding media having all essential amino acids for growth of a normal cell.

23. The method of claim 1, wherein the cancer is selected from the group consisting of acute lymphoblastic leukemia (ALL), chronic lymphoblastic leukemia (CLL), chronic myeloid leukemia (CML), acute myeloid leukemia (AML), Burkitt's lymphoma, non-small cell lung cancer (NSCLC), large cell lung cancer, squamous cell carcinoma, small cell lung cancer (SCLC), hepatocellular carcinoma (HCC), adenocarcinoma type of breast cancer, primary ductal carcinoma type of breast cancer, adenocarcinoma type of prostate cancer, bone metastatic from prostate carcinoma, hormone refractory prostate cancer, and colorectal carcinoma.

24. The method of claim 1, wherein the cancer is lung cancer, breast cancer, prostate cancer, colon cancer, lymphoma, or leukemia.

* * * * *